United States Patent [19]

Philion

[11] Patent Number: 4,695,589
[45] Date of Patent: * Sep. 22, 1987

[54] ALPHA-(AMINOALKYL-4-HYDROXY-3-(AL-KYLTHIO)BENZENEMETHANOLS

[75] Inventor: Richard E. Philion, Sand Lake, N.Y.

[73] Assignee: Sterling Drug Inc., New York, N.Y.

[*] Notice: The portion of the term of this patent subsequent to Feb. 15, 2000 has been disclaimed.

[21] Appl. No.: 499,102

[22] Filed: May 27, 1983

Related U.S. Application Data

[63] Continuation-in-part of Ser. No. 937,926, Aug. 30, 1978, abandoned, which is a continuation-in-part of Ser. No. 803,372, Jun. 3, 1977, abandoned, which is a continuation-in-part of Ser. No. 699,856, Jun. 25, 1976, abandoned.

[51] Int. Cl.⁴ ............................................. A01N 33/02
[52] U.S. Cl. .................... 514/653; 260/508; 514/544; 514/554; 514/654; 560/107; 560/110; 560/142; 564/344; 564/363; 564/364; 564/365; 564/366; 564/374; 564/381; 558/48

[58] Field of Search ....................... 564/363, 364, 365; 514/544, 648; 260/507, 508

[56] References Cited

U.S. PATENT DOCUMENTS

| | | | |
|---|---|---|---|
| 3,344,188 | 9/1967 | Wollweber et al. | 564/363 |
| 3,954,871 | 5/1976 | Buu-Hoi et al. | 260/570.6 |
| 4,374,149 | 2/1983 | Philion | 424/330 |

FOREIGN PATENT DOCUMENTS 1154193 6/1969 United Kingdom .

OTHER PUBLICATIONS

Lutz, et al., J. Med. Chem. 15, 795–802 (1972).

Primary Examiner—Robert V. Hines
Attorney, Agent, or Firm—Paul E. Dupont

[57] ABSTRACT

Alpha-(aminoalkyl)-4-hydroxy-3-(alkylthio)benzenemethanols useful as intermediates and as antihypertensive agents are prepared by reduction of the corresponding aminoalkyl 4-hydroxy-3-(alkylthio)phenyl ketones.

8 Claims, No Drawings

ALPHA-(AMINOALKYL-4-HYDROXY-3-(ALKYLTHIO)BENZENEMETHANOLS

CROSS-REFERENCE TO RELATED APPLICATIONS

This application is a continuation-in-part of copending application Ser. No. 937,926, filed Aug. 30, 1978, now abandoned, in turn a continuation-in-part of application Ser. No. 803,372, filed June 3, 1977, now abandoned, in turn a continuation-in-part of application Ser. No. 699,856, filed June 25, 1976 and now abandoned.

BACKGROUND OF THE INVENTION

1. Field of the Invention

The present invention relates to compositions of matter classified in the art of chemistry as α-(aminoalkyl)-4-hydroxy-3-(alkylthio)benzenemethanols and to a method of using the same for reducing blood pressure in mammals.

2. Information Disclosure Statement

Philion U.S. Pat. No. 4,374,149, issued Feb. 15, 1983 and pending Philion application Ser. No. 937,927, filed Aug. 30, 1978, disclose respective α-(aminoalkyl)-4-hydroxy-3-(alkylsulfinyl)benzenemethanols and α-(aminoalkyl)-4-hydroxy-3-(alkylsulfonyl)benzenemethanols.

Buu-Hoi et al. U.S. Pat. No. 3,954,871 issued May 4, 1976 (corresponds to Continental Pharma British Specification No. 1,321,701, published June 27, 1973, referred to in parent application Ser. No. 937,926) discloses a group of compounds embraced by the generic formula

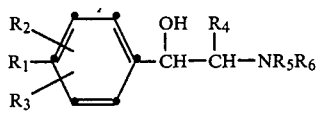

wherein, inter alia:

$R_1$ is RS, RSO or $RSO_2$ (R=H, or $C_1$–$C_{10}$ alkyl);

$R_2$ and $R_3$ are hydrogen, $C_1$–$C_4$ alkoxy or $C_1$–$C_4$ alkylthio;

$R_4$ is hydrogen or $C_1$–$C_4$ alkyl; and $R_5$ and $R_6$ are independently hydrogen or $C_1$–$C_{16}$ alkyl optionally substituted by a phenyl or substituted phenyl group.

The compounds are stated to exhibit β-adrenergic blocking, peripheral vasodilator, antiarrhythmic and hypotensive activities.

Lutz, et al., J. Med. Chem. 15, 795–802 (1972), disclose the attempted preparation of 4-hydroxy-3-mercaptophenylethanolamine, i.e.:

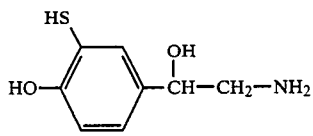

The compound however was neither isolated as a single entity nor characterized. Also disclosed is 4-hydroxy-3-mercaptophenylethylamine.

Pratesi, et al. British Specification No. 1,154,193, published June 4, 1969 discloses as a β-adrenergic agent α-[(isopropylamino)methyl]-3-(methylthio)benzenemethanol, i.e.:

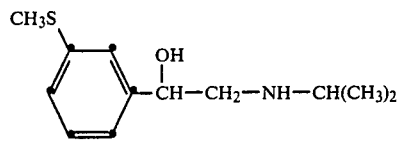

In the field of antihypertensive therapy the use of peripheral vasodilator agents to lower blood pressure has often suffered a serious disadvantage, namely, the reflex tachycardia elicited by the hypotension induced by systemic vasodilation. Recently efforts have been made to overcome this problem by employing hypotensive vasodilators in combination with β-adrenergic blocking agents, the function of the latter being to reduce the reflex tachycardia caused by the vasodilator-induced hypotension. This mode of therapy of course suffers the inconvenience of requiring two separate drugs and the attendant need for separate dosage regulation as well as the increased potential for patient error in failing to administer either one or the other of the drugs.

SUMMARY OF THE INVENTION

The present invention provides novel compounds which are useful as intermediates and as therapeutic agents. The compounds have both hypotensive vasodilator and β-adrenergic blocking activity and are therefore indicated for use as antihypertensive agents free of the undesirable tachycardic side effects associated with currently used vasodilator agents. Certain of the compounds also exhibit antiarrhythmic activity.

In a composition of matter aspect, the invention relates to certain α-{[(arylalkyl)amino]alkyl}-4-YO-3-(lower alkylthio)benzenemethanols which are useful as antihypertensive agents. Some species are also useful as antiarrhythmic agents. The compounds have further utility as intermediates for preparing the corresponding 3-lower alkylsulfinyl compounds of U.S. Pat. No. 4,374,149 which are also useful as antihypertensive agents.

In a method aspect the present invention provides a method of reducing blood pressure in mammals which comprises administering to said mammals a blood pressure lowering effective amount of an α-}[(arylalkyl)amino]alkyl}-4-YO-3-(lower alkylthio)benzenemethanol of the invention.

In another method aspect this invention relates to a method of producing vasodilation in mammals which comprises administering to said mammals, in an amount effective to produce vasodilation, an α{[(arylalkyl)amino]alkyl}-4-YO-3-(lower alkylthio)benzenemethanol of the invention.

DETAILED DESCRIPTION INCLUSIVE OF THE PREFERRED EMBODIMENTS

More specifically the invention sought to be patented resides, in a composition of matter aspect, in α-{[(arylalkyl)amino]alkyl}-4-YO-3-(lower alkylthio)benzenemethanols which are useful as intermediates and as antihypertensive agents and which have Formula I hereinbelow:

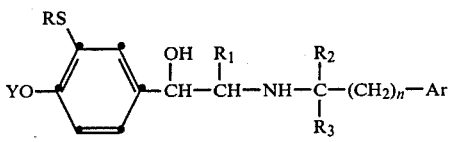

wherein:
- $R_1$, $R_2$ and $R_3$ are independently hydrogen or lower alkyl;
- n is an integer from 1 to 3;
- Ar is phenyl or phenyl having from one to three substituents selected from the group consisting of halo, lower alkyl, hydroxy and lower alkoxy;
- R is lower alkyl;
- Y is hydrogen, lower alkanoyl, aroyl, benzenesulfonyl or toluenesulfonyl;

and acid-addition salts thereof. As described more fully hereinbelow, certain of these compounds are also useful as antiarrhythmic agents.

Preferred embodiments within the ambit of the present invention are the compounds of Formula I above wherein Ar is phenyl or lower alkoxyphenyl, Y is hydrogen or lower alkanoyl and n is 1 or 2. These compounds exhibit good antihypertensive activity in the spontaneously hypertensive rat (SH Rat) as described hereinbelow.

A particularly preferred species is 4-hydroxy-α-<{[3-(4methoxyphenyl)-1-methylpropyl]amino}methyl>-3-(methylthio)benzenemethanol (Formula I: R and $R_2$ are each methyl; Y, $R_1$ and $R_3$ are each hydrogen; n is 2 and Ar is 4-methoxyphenyl). In addition to its antihypertensive activity this compound is an intermediate for preparing the corresponding 3-methylsulfinyl compound (USAN: sulfinalol hydrochloride) of U.S. Pat. No. 4,374,149 which compound is undergoing clinical evaluation as an antihypertensive agent in man.

In a method aspect the invention sought to be patented resides in the method of reducing blood pressure in mammals which comprises administering to said mammals a blood pressure lowering effective amount of a benzenemethanol of Formula I hereinabove.

In another method aspect the invention sought to be patented resides in the method of producing vasodilation in mammals which comprises administering to said mammals, in an amount effective to produce vasodilation, a benzenemethanol of Formula I hereinabove.

In the terms lower alkyl, lower alkoxy and lower alkylthio, "lower" denotes an alkyl moiety having from 1 to 4 carbon atoms which can be arranged as straight or branched chains. There are included methyl, ethyl, n-propyl, isopropyl, n-butyl, sec-butyl, and the like, methyl and ethyl being preferred.

By "lower alkanoyl" is meant straight or branched-chain alkanoyl radicals containing from 1 to 6 carbon atoms as illustrated by formyl, acetyl, propionyl, butyryl, isobutyryl, pivalyl, caproyl and the like.

The term "halo" as used herein denotes fluoro, chloro, bromo and iodo.

The term "aroyl" as used herein is intended to include benzoyl and benzoyl substituted by from one to two lower alkyl groups, for example: o-toluyl, p-toluyl, 3,4-dimethylbenzoyl, 3,5-dimethylbenzoyl, 2,5-dimethylbenzoyl, m-isopropylbenzoyl, p-tert-butylbenzoyl and the like.

It will be appreciated that Y in Formula I can represent acyl residues other than the above without departing from the spirit of the present invention since it is well known that such esters undergo hydrolytic cleavage under physiological conditions to produce in situ the parent phenols which, of course, have the previously indicated biological activity.

As used herein "toluenesulfonyl" is intended to include ortho, meta and para-toluenesulfonyl.

The 3-(lower alkylthio)benzenemethanols represented by Formula I hereinabove are obtained by reducing the aminoalkyl 3-(lower alkylthio)phenyl ketones of Formula II

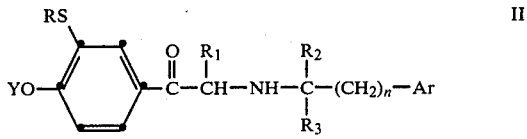

$^e$AED$_{50}$ = approximate intravenous dose required to cause 50% inhibition of the heart rate increase elicited by isoproterenol in the pentobarbitalized dog.
$^f$Actual reduction in blood pressure (in mm Hg) observed at the indicated dose.
$^g$Actual precentage reduction in blood pressure observed at the indicated dose.
$^h$Actual percentage inhibition of heart rate increase above control level observed at the indicated dose.

wherein R, $R_1$, $R_2$, $R_3$, n, Ar and Y have the above-given meanings, with an appropriate reducing agent in a suitable solvent as for example sodium borohydride or lithium borohydride in water or a lower alkanol; lithium aluminum hydride in ether, tetrahydrofuran or dioxane; diborane in tetrahydrofuran or diglyme; aluminum isopropoxide in 2-propanol; or by hydrogenation in the presence of a noble metal catalyst such as palladium or platinum.

When the aminoalkyl 3-(lower alkylthio)phenyl ketone contains a carboxylic ester group (Formula II wherein Y is lower alkanoyl or aroyl), and it is desired to retain the ester group in the reduction product (Formula I wherein Y is lower alkanoyl or aroyl), the use of reducing means resulting in reduction of carboxylic ester groups should of course be avoided. Accordingly, in such instances reduction is preferably effected with an alkali metal borohydride or by catalytic hydrogenation which reducing means result in selective reduction of the ketone function. When the ultimately desired product is the free phenol (Formula I wherein Y is hydrogen) the above reduction reaction can be followed by hydrolysis of the ester group, or alternatively, the esterified aminoalkyl 3-(lower alkylthio)phenyl ketone (Formula II wherein Y is lower alkanoyl or aroyl) can be reduced with a reagent capable of reducing both ketone and carboxylic ester functions e.g. lithium aluminum hydride.

The borohydride reduction method is conveniently carried out by treating the aminoalkyl phenyl ketone with sodium borohydride in methanol at about −10° C. to 65° C. for approximately 15 minutes to 2.5 hours or until reduction is substantially complete as indicated by thin layer chromatography. If the starting material contains an ester group (Formula II wherein Y is lower alkanoyl or aroyl) and it is desired to retain the latter in the final product, the reaction mixture is quenched with acid and the esterified benzenemethanol (Formula I wherein Y is lower alkanoyl or aroyl) is isolated in conventional fashion. If on the other hand, the free phenol (Formula I wherein Y is hydrogen) is desired the reaction mixture is treated with an equivalent of sodium or potassium hydroxide in water and stirred at about 20° C. to 65° C. for approximately 30 minutes to 15 hours. The resulting phenol is isolated in a conventional manner.

The catalytic hydrogenation process is conveniently carried out in a suitable solvent, for example N,N-dimethylformamide, at 20° C.-50° C. under a hydrogen pressure of from 20–50 p.s.i. in the presence of a noble metal catalyst such as palladium. The hydrogenation is continued until the theoretical amount of hydrogen is absorbed. After removal of the catalyst, the reduction product is isolated in conventional fashion.

The aminoalkyl 3-(lower alkylthio)phenyl ketones of Formula II hereinabove are obtained by reacting a haloketone of Formula III

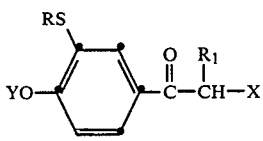

wherein R, $R_1$ and Y have the previously given meanings and X is chloro, bromo or iodo, with an excess of an (arylalkyl)amine of Formula IV

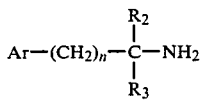

in a suitable solvent such as acetonitrile, dimethylsulfoxide or N,N-dimethylformamide at about $-65°$ C. to 25° C. for from 1 to 4 hours or until the reaction is substantially complete as indicated by thin layer chromatography.

In those instances wherein Y in Formula III is lower alkanoyl or aroyl, reaction with an (arylalkyl)amine may result in partial cleavage of the ester function. When desired, the partially deacylated product can be re-esterified according to known procedures for example with an acyl halide in the presence of a strong acid such as trifluoroacetic acid.

The (arylalkyl)amines of Formula IV are generally known, or if specifically new are obtained according to the procedures described for the preparation of the known compounds.

Thus for example tertiary carbinamines, i.e. (arylalkyl)amines of Formula IV wherein both $R_2$ and $R_3$ are lower alkyl can be obtained from the corresponding generally known tertiary carbinols via the well known Ritter reaction [Organic Reactions 17, 213 (1969)] followed by hydrolysis of the resulting tertiary carbinamides.

(Arylalkyl)amines of Formula IV wherein one of or both $R_2$ and $R_3$ are hydrogen can be obtained by reaction of an aldehyde or ketone of appropriate carbon content with ammonia or an ammonia derivative in accordance with the procedures described in Organic Reactions 4, 174 (1948) and Organic Reactions 5, 301 (1949).

The haloketones of Formula III are obtained by halogenating with chlorine or bromine the appropriate phenyl ketone having the Formula V hereinbelow:

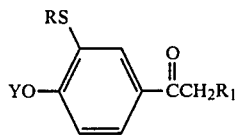

wherein R and $R_1$ have the previously given meanings and Y is lower alkyl, lower alkanoyl, aroyl, benzenesulfonyl or toluenesulfonyl. The reaction is conveniently carried out by treating the ketone of Formula V in an inert solvent such as chloroform with bromine at approximately 25° C. optionally in the presence of an inorganic base, e.g. calcium carbonate. The reaction generally has an induction period and in certain instances it may be advantageous to initiate the reaction by exposing the mixture to ultraviolet radiation until bromination has commenced as evidenced by decolorization and concomitant evolution of hydrogen bromide. If desired the Y substituent of the resulting haloketone can be removed according to well known procedures, for example, by ester hydrolysis when Y is lower alkanoyl or aroyl and by O-demethylation with a Lewis acid such as aluminum chloride, hydrogen bromide or boron tribromide when Y is methyl.

The corresponding iodoketones (Formula III wherein X is iodo) can be obtained by reacting the chloro or bromoketones with sodium or potassium iodide in acetone under the conditions of the well known Finkelstein reaction.

The phenyl ketones of Formula V hereinabove can be obtained by a variety of procedures which are generally known in the art.

Thus for example the 3-(lower alkylthio)phenyl ketones of Formula V wherein Y is lower alkanoyl or aroyl are obtained by alkylation of the parent 3-mercapto-4-hydroxyphenyl ketones (Formula V wherein R and Y are hydrogen) with an appropriate lower alkyl halide in a suitable solvent such as a lower alkanone in the presence of an acid acceptor, e.g. an alkali metal carbonate, followed by esterification of the resulting 3-(lower alkylthio)-4-hydroxyphenyl ketones (Formula V wherein R is lower alkyl and Y is hydrogen) with an appropriate acylating agent such as a lower alkanoyl or aroyl halide or anhydride in an inert solvent such as methylene chloride, chloroform, benzene or toluene in the presence of an acid acceptor such as triethylamine or pyridine. The 3-mercapto-4-hydroxyphenyl ketones are in turn obtained by chlorosulfonation of the generally known 4-hydroxyphenyl ketones with excess chlorosulfonic acid at about 0° C. to 25° C. preferably in the absence of a solvent followed by reduction of the resulting 3-chlorosulfonyl-4-hydroxyphenyl ketones with a suitable reducing agent such as stannous chloride and hydrochloric acid or zinc and sulfuric acid.

Alternatively, the 3-(lower alkylthio)phenyl ketones of Formula V can be obtained by acylating the generally known o-(lower alkylthio)phenols with an appropriate acyl halide (e.g. $R_1CH_2COCl$) under Friedel-Crafts conditions followed by esterification or alkylation of the resulting 3-(lower alkylthio)-4-hydroxyphenyl ketones.

Due to the presence of the basic amino grouping, the free base forms of the final products represented by Formula I react with organic and inorganic acids to form acid-addition salts. The compounds of the invention are useful both in the free base form and in the form of acid-addition salts, and both forms are within the purview of the invention. The acid-addition salts are simply a more convenient form for use, and in practice, use of the salt form inherently amounts to use of the base form.

The acid-addition salts are prepared from any organic or inorganic acid. They are obtained in conventional fashion, for instance either by direct mixing of the base with the acid, or, when this is not appropriate, by dissolving either or both the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acidaddition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, dibenzoyltartaric acid, oxalic acid, pyromucic acid, citric acid, lactic acid, mandelic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, cyclohexylsulfamic acid, isethionic acid, methanesulfonic acid, benzenesulfonic acid, p-toluenesulfonic acid, 1,4-naphthalenedisulfonic acid, butylarsonic acid, methanephosphonic acid, acidic resins, hydrofluoric acid, hydrochloric acid, hydrobromic acid, hydriodic acid, perchloric acid, nitric acid, sulfuric acid, sulfamic acid, glutaric acid, phosphoric acid, arsenic acid, and the like.

All the acid-addition salts are useful as sources of the free base form, by reaction with an inorganic base. It will thus be appreciated that if one or more of the characteristics such as solubility, crystallinity, molecular weight, physical appearance, toxicity, or the like of a given base or acid-addition salt thereof render that form unsuitable for the purpose at hand it can be readily converted, in accordance with procedures well known in the art, to another more suitable form.

When the compounds of the invention are to be utilized for pharmaceutical purposes, the acids used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from acids such as hydrochloric acid, acetic acid, lactic acid, tartaric acid, cyclohexylsulfamic acid, methanesulfonic acid, phosphoric acid and the like.

The compounds of the invention represented by Formula I wherein Y is hydrogen are of course amphoteric, having both acidic phenol and basic amino groups, and thus form salts with both acids and bases.

Due to the presence of at least one and as many as three asymmetric centers in the compounds of the invention represented by Formula I (i.e. the carbinol carbon atom, the carbon atom to which $R_1$ when loweralkyl is attached and the carbon atom to which $R_2$ and $R_3$ when dissimilar are attached) said compounds can exist in as many as 8 stereochemically isomeric forms, all of which either individually or as mixtures of any two or more are considered within the purview of this invention. If desired, the isolation or the production of a particular stereochemical form or of a mixture of two or more stereochemical forms can be accomplished by application of general principles known in the art.

When preparing either a particular stereoisomer or a specific mixture of any two or more stereoisomers it is advantageous to employ intermediates of fixed stereochemical configuration thereby limiting the number of stereo-isomeric forms present in the final product and thus simplifying isolation of the desired components. Accordingly prior to reaction with a haloketone of Formula III an (arylalkyl)amine of Formula IV containing an asymmetric center (i.e. the carbon bearing nonidentical substituents $R_2$ and $R_3$) is resolved into its (+) and (−) optical antipodes according to conventional techniques and employing conventional resolving agents such as optically active tartaric acid, O,O-dibenzoyl tartaric acid, mandelic acid, malic acid, and the like. As desired, either the (+) or the (−)-(arylalkyl)amine can then be reacted with a haloketone according to the previously described procedure to produce an aminoalkyl phenyl ketone of Formula II having a fixed stereochemical configuration at the carbon bearing substituents $R_2$ and $R_3$.

When the haloketone also contains an asymmetric center (Formula III wherein $R_1$ is alkyl) reaction with either the (+) or (−)-arylalkyl)amine produces a pair of diastereomeric aminoalkyl phenyl ketones of Formula II ($R_1$ is lower alkyl) which can be separated according to conventional methods, e.g. fractional crystallization of a suitable acid addition salt.

Of course when the haloketone contains no asymmetric center (Formula III wherein $R_1$ is hydrogen) reaction with either the (+) or (−)-(arylalkyl)amine produces directly a single (+) or (−) stereoisomer of the aminoalkyl phenyl ketone of Formula II ($R_1$ is hydrogen).

Reduction of the stereochemically fixed aminoalkyl phenyl ketone as described hereinabove creates a new asymmetric center (i.e. the carbinol carbon atom) and therefore produces a pair of diastereomeric 3-(lower alkylthio)benzenemethanols of Formula I. If desired the diastereomers can be separated according to known methods, for example, by fractional crystallization of the acid-addition salt of an optically active acid such as (+) or (−) mandelic acid, tartaric acid, O,O-dibenzoyltartaric acid, malic acid and the like, or by converting the diastereomeric mixture to a suitable ester derivative (i.e. Y in Formula I is lower alkanoyl, aroyl, benzenesulfonyl or p-toluenesulfonyl) e.g. the acetate, benzoate, or p-toluenesulfonate and separating the esters by chromatography or by fractional crystallization of a suitable acid-addition salt thereof.

The compounds of the present invention having Formula I hereinabove exhibit useful antihypertensive, vasodilator and β-adrenergic blocking activity. Of particular advantage is the combination in a single compound of vasodilator and β-adrenergic blocking activity whereby the reflex tachycardia associated with the reduction in blood pressure through vasodilation is effectively reduced or eliminated by β-adrenergic blockade. The compounds are therefore effective in lowering blood pressure without causing undesirable tachycardic effects.

It should be noted, however, that although both vasodilator and β-adrenergic blocking activity reside in the same compound, the time of onset of each of these actions appears to be somewhat different, vasodilation usually preceding β-adrenergic blockade. This can of course give rise to a moderate transient increase in heart rate observable on the first day or two of repeated medication. Thereafter, however, β-adrenergic blockade takes full effect and subsequent continuous medication effects sustained blood pressure lowering with no appreciable elevation of heart rate. Moreover as opposed to the antihypertensive response which is directly dose-related, the heart rate elevation observed at the lower doses tested is not appreciably increased either in magnitude or in duration at higher doses. It is therefore possible to raise the dosage level in order to achieve a further reduction in blood pressure without causing a corresponding increase in heart rate.

In carrying out the method aspect of this invention, i.e. the method of reducing hypertension in mammals which comprises administering to said mammals an antihypertensively effective amount of a compound having Formula I said compound can be administered orally in the form of a pill, tablet, capsule, e.g. in admixture with talc, starch, milk sugar or other inert, i.e. non-toxic or pharmacologically acceptable pharmaceutical carrier, or in the form of an aqueous solution, suspension, encapsulated suspension, gel, elixir, aqueous alcoholic solution, e.g. in admixture with sugar or other sweetening agents, flavorings, colorants, thickeners and other conventional pharmaceutical excipients. When injected subcutaneously, intramuscularly, or intravenously, it can be administered, e.g., as an aqueous or peanut oil solution or suspension using excipients and carriers conventional for this mode of administration. The best route of administration and the best dosage will be apparent from the laboratory tests for activity and toxicity of the selected compound conventionally undertaken as part of the development phase of a pharmaceutical. Ordinarily an oral dosage unit contains about 1 to 50 mg. of the active medicament and is administered as often as required to maintain blood pressure reduction, e.g. 1 to 3 times daily.

The 3-lower alkylthio compounds of Formula I are also useful as intermediates in the preparation of the corresponding 3-lower alkylsulfinyl compounds which are of particular value as antihypertensive agents. The 3-lower alkylthio compounds are converted to the corresponding 3-lower alkylsulfinyl compounds as described in detail in U.S. Pat. No. 4,374,149.

The molecular structures of the compounds of the invention were assigned on the basis of the method of their preparation and study of their IR and NMR spectra, and confirmed by the correspondence between calculated and found values for the elemental analyses of representative examples.

The identity and purity of individual stereoisomers as well as the composition of stereoisomeric mixtures were determined on the basis of optical rotation and high pressure liquid chromatography.

The invention is illustrated by the following examples without, however, being limited thereto. Unless otherwise specified optical rotations were determined on a 2% solution of the compound in methanol.

EXAMPLE 1

A. To 100 g. (0.085 mole) of chlorosulfonic acid at 5° C. was added over a period of 25 minutes 20 g. (0.15 mole) of p-hydroxyacetophenone. The temperature was allowed to gradually rise to 22° C. as the reaction was stirred overnight. The temperature was then raised to 55°-60° C. and stirring was continued an additional hour. The reaction mixture was quenched in ice-water and the precipitated solid was collected and washed with water. The product was dissolved in ethyl acetate and the resulting solution was dried and evaporated to dryness. The residue was recrystallized from benzene to give 12.5 g. of 4'-hydroxy-3'-(chlorosulfonyl)acetophenone, m.p. 138°-142° C. The filtrate afforded a second crop of 5.0 g., m.p. 124°-136° C.

B. Hydrogen chloride was bubbled into a stirred mixture containing 105 g. (0.46 mole) of stannous chloride dihydrate and 400 ml. of glacial acetic acid until a nearly clear solution was obtained. To the latter solution was added portionwise over 20 minutes 18 g. (0.077 mole) of crude 440 -hydroxy-3'-(chlorosulfonyl)acetophenone while the temperature was maintained at 25°-30° C. After the addition was complete sitrring was continued an additional 0.5 hours. The reaction mixture was then poured into 400 ml. of 12N hydrochloric acid, diluted with 800 ml. of water and extracted with chloroform. The extracts were washed with saturated aqueous sodium chloride and evaporated to dryness. The residue was recrystallized from benzene to give 4 g. of 4-hydroxy-3'-mercaptoacetophenone, m.p. 117°-120° C.

C. A mixture containing 1.0 g. (0.006 mole) of 4'-hydroxy-3'-mercaptoacetophenone, 0.9 g. (0.0063 mole) of methyl iodide, 0.83 g. (0.006 mole) of potassium carbonate and 12 ml. of acetone was stirred 2.5 hours at room temperature. The reaction mixture was filtered and the filtrate evaporated to dryness. The residue was dissolved in chloroform and the resulting solution was washed with 1N hydrochloric acid, dried over anhydrous sodium sulfate and evaporated to dryness. The residue was dissolved in hot benzene and the solution was filtered through a ¼" pad of silica gel in order to remove a colored impurity. Evaporation of the filtrate afforded 0.9 g. of 4'-hydroxy-3'-(methylthio)acetophenone, m.p. 117°-120° C.

D. Alternatively, to a stirred solution containing 61.4 g. (0.435 mole) of o-(methylthio)phenol and 35 g. (0.45 mole) of acetyl chloride in 170 ml. of nitrobenzene was added portionwise over a period of 20 minutes 80 g. (0.60 mole) of aluminum chloride. The reaction mixture was stirred overnight at room temperature and then one hr. at 65° C. The reaction mixture was cooled, diluted with ice and water and extracted with methylene chloride. The organic extracts were evaporated in vacuo, the residue diluted with ether and allowed to stand two days in the refrigerator. The precipitated product was collected and dried to give 27 g. of 4'-hydroxy-3'-(methylthio)acetophenone.

E. To a cooled, stirred solution containing 24.5 g. (0.134 mole) of 4'-hydroxy-3'-(methylthio)acetophenone and 21 g. (0.21 mole) of triethylamine in 400 ml. of methylene chloride was added dropwise over a period of 30 minutes 16.4 g (0.21 mole) of acetyl chloride. After stirring overnight at room temperature the reaction mixture was washed with water, dried over anhydrous sodium sulfate, and concentrated to a small volume. The concentrate was diluted with ether and cooled in an ice bath. The resulting precipitate was collected to give 23.5 g. of 4'-hydroxy-3'-(methylthio)acetophenone 4'-acetate.

F. To a stirred mixture containing 23.2 g. (0.108 mole) of 4'-hydroxy-3'-(methylthio)acetophenone 4'-acetate and 9 g. of calcium carbonate in 300 ml. of chloroform was added dropwise over a period of two hours a solution containing 6 ml. (0.108 mole) of bromine in 30 ml. of chlorofom. The reaction mixture was filtered, and the filtrate washed with saturated aqueous sodium bicarbonate, and evaporated to dryness. The residue was dissolved in ether and the ethereal solution diluted with cyclohexane and cooled in ice. The resulting precipitate was collected and dried to give 26.5 g. of 2-bromo-4'-hydroxy-3'-(methylthio)acetophenone 4'-acetate.

G. To a stirred solution containing 16.5 g. (0.10 mole) of 2-(4-methoxyphenyl)-1-methylethylamine and 5 g. (0.051 mole) of triethylamine in 40 ml. of N,N-dimethylformamide at −65° C. was added dropwise over a period of 2 hours 15.5 g. (0.051 mole) of 2-bromo-4'-hydroxy-3'-(methylthio)acetophenone 4'-acetate in 40 ml. of N,N-dimethylformamide. After the addition was complete stirring at −65° C. was continued an additional hour. The reaction mixture was then acidified with 10 ml. of 12N hydrochloric acid and diluted with 100 ml. of water. Upon shaking the aqueous solution with 200 ml. of a 2:1 mixture of ether-methylene chloride the product begin to precipitate from the aqueous phase. The layers were separated and the aqueous portion was cooled in ice. The resulting precipitate was collected and dried 3 hours over phosphorous pentoxide in a 65° vacuum oven to give 12.1 g. of 4'-hydroxy-2-{[2-(4-methoxyphenyl)-1-methylethyl]amino}-3'-(methylthio)acetophenone 4'-acetate hydrochloride.

EXAMPLE 2

A stirred solution containing 12.5 g. (0.029 mole) of 4'-hydroxy-2-{[2-(4-methoxyphenyl)-1-methylethyl]amino}-3'-(methylthio)acetophenone 4'-acetate hydrochloride in 200 ml. of methanol was cooled in an ice-acetone bath and treated portionwise over 15 minutes with 0.9 g. of sodium borohydride. After the addition was complete stirring was continued an additional 20 minutes. The reaction mixture was then brought to pH 7 with glacial acetic acid and evaporated to dryness. The residue was diluted with ether and washed thoroughly with saturated aqueous sodium bicarbonate. The ethereal solution was dried over anhydrous sodium sulfate and concentrated to a small volume. The concentrate was acidified with ethereal hydrogen chloride and cooled overnight in a refrigerator. The precipitated product was collected and recrystallized from methanolisopropyl alcohol to give 2.1 g. of 4-hydroxy-α-<{[2-(4-methoxyphenyl-1-methylethyl]amino}methyl>-3-(methylthio)benzenemethanol 4-aceetate hydrochloride, m.p. 143°–145° C.

In addition to its antihypertensive activity this compound was also found to possess β-adrenergic stimulant activity as evidenced by its ability to block histamine-induced bronchoconstriction in the dog.

EXAMPLE 3

To a stirred suspension of 6.9 g. (0.016 mole) of 4'-hydroxy-2-{[2-(4-methoxyphenyl)-1-methylethyl]amino}-3'-(methylthio)acetophenone 4'-acetate hydrochloride in 120 ml. of methanol was added 400 mg. of sodium borohydride. After 25 minutes all the starting material had gone into solution. The reaction mixture was treated with 10 ml. of water and stirred overnight at room temperature. A solution containing 900 mg. of potassium hydroxide in 10 ml. of water was then added and the mixture heated under reflux 0.5 hour. The resulting solution was concentrated to one half volume, the concentrate made slightly acidic with 12N hydrochloric acid and evaporated nearly to dryness. The residue was diluted with saturated aqueous sodium bicarbonate and extracted with ethyl acetate. The organic extracts were dried over anhydrous sodium sulfate, acidified with glacial acetic acid, and concentrated until crystallization began. The product was collected, tritrated with chloroform and finally recrystallized from chloroformmethanol to give 3.9 g. of 4-hydroxy-α-<{[2-(4-methoxyphenyl)-1-methylethyl]amino}methyl>-3-(methylthio)benzenemethanol acetate salt, m.p.163°–165° C.

EXAMPLE 4

To a stirred solution containing 24 g. (0.135 mole) of 3-(4methoxyphenyl)-1-methylpropylamine in 40 ml. of N,N-dimethylformamide at −50° C. was added dropwise over 15 minutes a solution containing 15 g. (0.05 mole) of 2-bromo-4'-hydroxy-3'-(methylthio)acetophenone 4'-acetate in 35 ml. of N,N-dimethylformamide. After the addition was complete stirring was continued an additional 1.25 hours. The reaction mixture was then treated with 4 ml. of 12N hydrochloric acid, diluted with 100 ml. of water and extracted with ether-ethyl acetate. The organic extracts were dried over anhydrous sodium sulfate, acidified with ethanolic hydrogen chloride and evaporated to dryness. The crude product containing both the 4'-acetate and 4'-hydroxy compounds was dissolved in a solution containing 10 ml. of acetyl chloride in 120 ml. of trifluoroacetic acid and stirred 2 hours at room temperature. The solution was then evaporated to dryness and the residue partitioned between ether and water. The ether layer was dried over anhydrous sodium sulfate and acidified with ethanolic hydrogen chloride. The resulting precipitate was collected and triturated with acetone-ether to give 6.0 g. of 4'-hydroxy-2-{[(3-(4-methoxyphenyl)-1-methylpropyl]amino}-3'-(methylthio)acetophenone 4-acetate hydrochloride, m.p. 160°–165° C.

EXAMPLE 5

To a stirred mixture of 9.0 g. (0.021 mole) of 4'-hydroxy-2{[3-(4-methoxyphenyl)-1-methylpropyl]amino}-3'-(methylthio)acetophenone 4'-acetate hydrochloride and 100 ml. of methanol at −5° to 0° C. there was added portionwise 0.5 g. (0.015 mole) of sodium borohydride. After stirring an additional 0.5 hour, a solution containing 1.0 g. of potassium hydroxide in 10 ml. of water was added and the resulting mixture was stirred at room temperature under nitrogen overnight, and then at reflux 0.5 hour. The pH was adjusted to 7 with glacial acetic acid and the resulting solution was concentrated to a small volume, diluted with saturated aqueous sodium bicarbonate and extracted with ethyl acetate. The ethyl acetate solution was dried over anhydrous sodium sulfate, acidified with glacial acetic acid, concentrated to a small volume and cooled. The product which separated was collected and recrystallized from ethyl acetate-ethanol affording 7.2 g. of 4-hydroxy-α-<{[3-(4-methoxyphenyl)-1-methylpropyl]amino}methyl>-3 -(methylthio)benzenemethanol acetate salt, m.p. 132°–134° C.

EXAMPLE 6

A. To a stirred solution containing 100 g. (0.55 mole) of 4'-hydroxy-3'-(methylthio)acetophenone in 600 ml. of pyridine at 15°–18° C. there was added dropwise over one hour 68 ml. (0.58 mole) of benzoyl chlorie. After addition was complete stirring was continued at room temperature for 1.5 hours. The reaction mixture was then quenched in 1.5 liters of ice-cold water. The solid which precipitated was collected by filtration, washed successively with water, cold 2-propanol, and n-hexane and dried to give 146 g. of 4'-hydroxy-3'-(methyltho)acetophenone 4'-benzoate, m.p. 126°–131° C.

B. To a stirred suspension containing 145 g. (0.51 mole) of 4'-hydroxy-3'-(methylthio)acetophenone 4'-benzoate in 1200 ml. of benzene at 20° C. was added 15 ml. of a solution containing 85 g. (0.53 mole) of bromine in 100 ml. of benzene. The mixture was irradiated with uv light for about 1 hour in order to initiate the reaction. When the reaction commenced (as indicated by decolorization) a slow stream of nitrogen was bubbled through the reaction mixture and the remainder of the bromine solution was added over a period of 2 hours while the temperature was maintained at 20°–24° C. The reaction mixture was stirred an additional 0.5 hour and then cooled to 16° C. The solid which precipitated was collected by filtration, washed with water and n-hexane, and dried to give 90 g. of 2-bromo-4'-hydroxy-3'-(methylthio)acetophenone 4'-benzoate, m.p. 127°–129° C. The benzene solution afforded an additional 21 g. of product m.p. 126°–129° C.

C. To a stirred solution containing 36 g. (0.2 mole) of 3-(4-methoxyphenyl)-1-methylpropylamine in 175 ml. of N,N-dimethylformamide at −60° C. was added over one hour a solution containing 25 g. (0.068 mole) of 2-bromo-4'-hydroxy-3'-(methylthio)acetophenone 4'-benzoate in 120 ml. of N,N-dimethylformamide. After the addition was complete stirring at −60° C. was continued an additional 20 minutes. The reaction mixture was then diluted with 200 ml. of chloroform, treated with 20 ml. of 45% hydrogen bromide and further diluted with 200 ml. of cold water. The layers were separated and the aqueous layer was re-extracted with chloroform. The organic layers were combined, washed with water, dried over anhydrous magnesium sulfate and concentrated to about 100 ml. The concentrate was diluted with 400 ml. of ether and cooled. The resulting precipitate was collected by filtration, washed successively with cold 2-propanol and ether and dried to give 26 g. of 4'-hydroxy-2-{[3-(4-methoxyphenyl)-1-methylpropyl]amino}-3'-(methylthio)acetophenone 4'-benzoate hydrobromide.

EXAMPLE 7

To a stirred mixture of 25 g. (0.046 mole) of 4'-hydroxy-2-{[3-(4-methoxyphenyl)-1-methylpropyl]amino}-3'-(methylthio)acetophenone 4'-benzoat hydrobromide and 160 ml. of methanol at 0° C. was added portionwise over 0.5 hour 1.4 g. (0.037 mole) of sodium borohydride. After stirring an additional 20 minutes the reaction mixture was treated with a solution containing 2.5 g. of potassium hydroxide in 30 ml. of water and heated under reflux 40 minutes. The reaction mixture was concentrated in vacuo until a cloudy suspension formed. The suspension was brought to pH 3 with 6N hydrochloric acid and then made basic with saturated aqueous sodium bicarbonate. The remaining methanol was removed by evaporation in vacuo. The resulting suspension was diluted with 200 ml. of ethyl acetate and the resulting biphasic mixture was allowed to stand overnight. The solid which precipitated was collected, washed with water followed by n-pentane and recrystallized from 2-propanol to give 6 g. of 4-hydroxy-α-<{[3-(4-methoxyphenyl)-1-methylpropyl]amino}methyl>-3-(methylthio)benzenemethanol, m.p. 126°–129° C.

The ethyl acetate layer in the filtrate was separated, washed successively with dilute aqueous sodium bicarbonate and water, and dried over anhydrous magnesium sulfate. The resulting solution was diluted with 120 ml. of isopropyl acetae, treated with 3 ml. of glacial acetic acid, seeded and cooled. The resulting precipitate was collected, washed with isopropyl acetate and dried at 65° C. in vacuo affording 7 g. of product as the acetate salt, m.p. 132°–134° C.

EXAMPLE 8

A. To a stirred solution containing 376 g. (1.0 mole) of (−)-dibenzoyltartaric acid in a mixture of 5 l. of methanol and 550 ml. of water at 42° C. there was added 179 g. (1.0 mole) of (±)-3-(4-methoxyphenyl)-1-methylpropylamine. The mixture was stirred 26 hours at 40° C. and then 20 hours at room temperature. The resulting precipitate was collected and dried affording a first crop of 176.5 g. of (−)-3-(4-methoxyphenyl)-1-methylpropylamine (−)-dibenzoyltartrate salt, m.p. 175°–176° C. (dec.), $[\alpha]_D^{25} = -88.0°$. By cooling the filtrate at 0° C. for 7 hours a second crop of 58.5 g. was obtained, m.p. 167°–171° C. (dec.), $[\alpha]_D^{25} = -86.3°$. The final mother liquors were set aside for use in part B below. The first crop was recrystallized from 90% methanol to give 145.3 g., m.p. 179°–180.5° C. $[\alpha]_D^{25} = -87.5°$. This salt was treated with aqueous sodium hydroxide and the liberated amine extracted into chloroform. The chloroform extracts were dried over anhydrous potassium carbonate and evaporated to dryness. The residual oil was dissolved in 2-propanol, the resulting solution acidified with 25 ml. of 12N hydrochloric acid, and evaporated to dryness. The solid residue was dried, recrystalized from 2-propanol and dried again to give 52.0 g (−)-3-(4-methoxyphenyl)-1-methylpropylamine hydrochloride, m.p. 126°–129° C., $[\alpha]_D^{25} = -6.0°$ (2% in water).

B. The mother liquors remaining after isolation of (−)-3-(4-methoxyphenyl)-1-methylpropylamine (−)-dibenzoyltartrate salt were concentrated to a volume of 500 ml. and cooled at 0° C. for 2 hours. The resulting precipitate was collected and dried to give 283 g. of (+)-3-(4-methoxyphenyl)methylpropylamine (−)-dibenzoyltartrate salt, m.p. 159°–162° C. (dec.). This salt was treated with aqueous sodium hydroxide and the liberated amine extracted into chloroform. Evaporation of the chloroform left 80 g. of oil which was then added to a solution containing 168 g. of (+)-dibenzoyltartaric acid in 1860 ml. of 90% methanol. After stirring 20 hours at room temperature the precipitated salt was collected and dried affording 173.5 g. of (+)-3-(4-methoxyphenyl)-1-methylpropylamine (+)-dibenzoyltartrate, m.p. 179°–180° C. (dec.), $[\alpha]_D^{25} = +87.1°$. Recrystallization from 90% methanol afforded 149 g., m.p. 181° C. (dec.), $[\alpha]_D^{25} = +90.3°$ Following the procedure described in part A the amine was liberated from the (+)-dibenzoyltartrate salt and converted to the hydrochloride to give 55.0 g. of (+)-3-(4-methoxyphenyl)-1-methylpropylamine hydrochloride, m.p. 127°–130° C., $[\alpha]_D^{25} = +5.6°$ (2% in water). The nmr spectrum of this product in the presence of the shift reagent tris[(trifluoromethyl)hydroxymethylene-α-camphorato]europium III, Eu(TFC)₃ indicated contamination by approximately 10–15% of the levo isomer.

C. (+)-3-(4-Methoxyphenyl)-1-methylpropylamine (−)-dibenzoyltartrate salt (8781 g.) prepared according to part B above was recrystallized from aqueous methanol to give 7690 g., m.p. 163°–165° C. A 700-gram sample was recrystallized twice from aqueous methanol affording 558 g. of the salt which was then converted to the free amine and distilled under reduced pressure to give 180.5 g. of (+)-3-(4-methoxyphenyl)-1-methylpropylamine, b.p. 88°–100° C./0.1 mm. The nmr spectrum of this productin the presence of the shift reagent Eu(TFC)₃ indicated an optical purity ≧97%.

D. Alternatively (+)-3-(4-methoxyphenyl)-1-methylpropylamine was obtained as follows:

A solution of 300 g. (1.67 moles) of dl-3-(4-methoxyphenyl)-1-methylpropylamine in 2 l of 95% ethanol was added in one portion to a stirred warm solution (40°–45° C.) of 250 g. (1.67 moles) of d-tartaric acid in 2.6 l of water and 4.2 l of 95% ethanol. The clear solution was seeded at about 38° C. and was then allowed to come to room temperature overnight with stirring. The crystallized solid was filtered and pressed thoroughly with a rubber dam; it was washed twice with enough ice-cold 8% aqueous ethanol to cover the cake and was thoroughly pressed dry. The product was dried at 60° in vacuo for five hours to afford 276 g. of crude d-amine bitartrate, m.p. 181°–182° C. Five recrystallizations from aqueous ethanol afforded 125 g. of the bitartrate, m.p. 188°–190° C. The optical purity of the liberated (+)-3-(4-methoxyphenyl)-1-methylpropylamine was shown to be ≧97%.

EXAMPLE 9

To a stirred solution containing 35.7 g. (0.172 mole) of incompletely resolved (−)-3-(4-methoxyphenyl)-1-methylpropylamine hydrochloride, $[\alpha]_D^{25} = -6.0°$ (2% in water) in 125 ml. of N,N-dimethylformamide was added 25 ml. of triethylamine causing immediate precipitation of triethylamine hydrochloride. The mixture was stirred 20 minutes and then cooled to −50° C. The remainder of the preparation was carried out following a procedure similar to that of example 7 but using 20 g. (0.66 mole of 2-bromo-4'-hydroxy-3'-(methylthio)acetophenone 4'-acetate and 8 ml. of acetyl chloride to give 15 g. of incompletely resolved (−)-4'-hydroxy-2-{[3-(4-methoxyphenyl)-1-methylpropyl]amino}-3'-(methylthio)acetophenone 4'-acetate hydrochloride, m.p. 179°–181° C., $[\alpha]_D^{25} = -10.3°$.

EXAMPLE 10

To a stirred solution containing 12 g. (0.027 mole) of incompletely resolved (−)-4'-hydroxy-2-{[3-(4-methoxyphenyl)-1-methylpropyl]amino}-3'-(methylthio)acetophenone 4'-acetate hydrochloride (m.p. 179°–181° C., $[\alpha]_D^{25} = -10.3°$) in 150 ml. of methanol at 0° C., was added portionwise 0.8 g. (0.020 mole) of sodium borohydride. After stirring an additional 15 minutes, a solution containing 1.6 g. of potassium hydroxide in 25 ml. of water was added and the resulting mixture was heated at reflux under nitrogen 0.5 hours. The reaction mixture was concentrated to a small volume, acidified with 3N hydrochloric acid, then made basic with saturated aqueous sodium bicarbonate and extracted with ethyl acetate. After drying over anhydrous sodium sulfate the ethyl acetate solution was evaporated to drynes leaving 11 g. of pale yellow oil. This oil was dissolved in 200 ml. of ethyl acetate and a 40 ml aliquot was adsorbed on a column of silica gel and the product eluted with 92:8 ethyl acetate-methanol to give 1.7 g. of oil which was converted to the acetate salt affording 1.22 g. of levorotatory 4-hydroxy-α-<{[3-(4-methoxyphenyl)-1-methylpropyl]amino}methyl<3-(methylthio)benzenemethanol acetate salt, m.p. 124°–125° C., $[\alpha]_D^{25} = -6.4°$.

EXAMPLE 11

A. Following a procedure similar to that described in Example 9 but using 43 g. (0.20 mole) of incompletely resolved (+)-3-(4-methoxyphenyl)-1-methylpropylamine hydrochloride, $[\alpha]_D^{25} = +5.6°$ (2% in water) and 23 g. (0.077 mole) of 2-bromo-4'-hydroxy-3'-(methylthio)acetophenone 4'-acetate there was obtained 17.1 g. of incompletely resolved (+)-4'-hydroxy-2-{[3-(4-methoxyphenyl)-1-methylpropyl]amino}-3'-(methylthio)acetophenone 4'-hydrochloride, m.p. 178°–180° C., $[\alpha]_D^{25} = +10.2°$.

B. Following a procedure similar to the above but acidifying the reaction mixture with 48% hydrogen bromide in place of 12N hydrochloric acid and omitting the reactylation step afforded, after recrystallization twice from chloroform-isopropyl acetate and once from chloroform-acetone, incompletely resolved (+)-4'-hydroxy-2-{[3-(4-methoxyphenyl)-1-methylpropyl]amino}-3'-(methylthio)acetophenone 4'-acetate hydrobromide, m.p. 182°–183° C., $[\alpha]_D^{25} + 9.0°$.

EXAMPLE 12

A. Following a procedure similar to that described in Example 10 but using 17.1 g. (0.039 mole) of (+)-4'-hydroxy-2-{[3-(4-methoxyphenyl)-1-methylpropyl]amino}-3'-(methylthio)acetophenone 4'-acetate hydrochloride (m.p. 178°–180° C., $[\alpha]_D^{25} = +10.2°$), 1.0 g. (0.025 mole) of sodium borohydride and 2.0 g. of potassium hydroxide there was obtained 15 g. of 4-hydroxy-α<{[3-(4-methoxyphenyl)-1-methylpropyl]amino}methyl>3-(methylthio)benzenemethanol as a dextrorotatory pair of diastereomeric benzenemethanols. A 3.0-gram sample was dissolved in isopropyl acetate and the resulting solution acidified with glacial acetic acid. The product was allowed to crystallize slowly over 2 days to give 2.75 g. of crystalline acetate salt, m.p. 124°–126° C., $[\alpha]_D^{25} = +7.7°$.

B. When a procedure similar to the above was carried out using (+)-4'-hydroxy-2-{[3-(4-methoxyphenyl)-1-methylpropyl]amino}-3'-(methylthio)-acetophenone 4'-acetate hydrobromide m.p. 182°–183° C., $[\alpha]_D^{25} + 9.0°$ there was obtained dextrorotatory 4-hydroxy-α-<{[3-(4-methoxyphenyl)-1-methylpropyl]amino}methyl>3-(methylthio)benzenemethanol acetate salt, m.p. 128°–129.5° C., $[\alpha]_D^{25} = +5.6°$.

C. Following a procedure similar to that described in Example 7 but employing 40 g. (0.0758 mole) of optically pure (+)-4'-hydroxy-2-{[3-(4-methoxyphenyl)-1-methylpropyl]amino}-3'-(methylthio)acetophenone 4'-benzoate hydrobromide (m.p. 171°–175° C., $[\alpha]_D^{25} = +11.8°$) prepared according to Example 14B hereinbelow, 1.5 g. of sodium borohydride and 4.5 g of potassium hydroxide there was obtained 25.1 g. of 4-hydroxy-α<{[3-(4-methoxyphenyl)-1-methylpropyl]amino}methyl>-3-(methylthio)benzenemethanol acetate salt, m.p. 125°–127° C., $[\alpha]_D^{25} = +7.3°$, as a dextrorotatory pair of diastereomeric benzenemethanols. Another similar run afforded a product with m.p. 129°–130° C., $[\alpha]_D^{25} = +7.1°$. The hydrochloride had m.p. 153°–155° C. Another run produced a hydrochloride m.p. 155°–157° C. $[\alpha]_D^{25} = +8.8°$.

The pair of diastereomeric benzenemethanols of this Example correspond to the products of Examples 13C and 17.

EXAMPLE 13

A. A solution containing 10.5 g. of dextrorotatory 4-hydroxy-α-<{[3-(4-methoxypnenyl)-1-methylpropyl]amino}methyl>-3-methylthio)benzenemthanol prepared as described in Example 12A and 2.25 g. of (−)-mandelic acid in 60 ml. of isopropyl acetate was stirred 4.5 hours. The precipitated solid was collected to give 3.7 g. of white crystalline solid, m.p. 99°–100° C., $[\alpha]_D^{25} = -20.9°$ which was labeled "solid A" and set aside. The filtrate was washed with saturated aqueous sodium bicarbonate, dried over anhydrous sodium sulfate and evaporated to dryness. The residual 6 g. of gum was dissolved in 40 ml. of isopropyl acetate and treated with a solution of 2.0 g. of (+)-mandelic acid in 20 ml. of isopropyl acetate and the resulting solution stirred overnight. The precipitated product was collected giving 4.1 g. of tan crystalline solid m.p. 89°–93°, $[\alpha]_D^{25} +35.4°$. The filtrate was labeled "filtrate A" and set aside. The solid was recrystallized by dissolving in 55 ml. of 10:1 isopropyl acetate-isopropyl alcohol and stirring overnight. After removing a small amount of solid impurity the clear solution was concentrated to a volume of 30 ml. whereupon the product crystallized to give 1.6 g. of tan crystals m.p. 89°–106°, $[\alpha]_D^{25} = +48.7°$ which was labeled "solid B" and set aside. The filtrate was labeled "filtrate B".

"Filtrate A" was washed with saturated aqueous sodium bicarbonate, dried over anhydrous sodium sulfate and evaporated to dryness. The resulting 4.0 g. of yellow gum was dissolved in 40 ml. of ethyl acetate and treated with 1.0 g of (−)-mandelic acid. After standing overnight the precipitated product was collected to give 2.5 g. of crystalline solid m.p. 108°–110.5° C., $[\alpha]_D^{25} = -33°$ which was labeled "solid C" and set aside. The filtrate was combined with "filtrate B" above and evaporated to dryness, and the residue combined with "solid A". The combined materials were dissolved in ethyl acetate, the resulting solution washed with saturated aqueous sodium bicarbonate, dried over anhydrous sodium sulfate and evaporated to dryness. The residual 6.4 g. of yellow syrup was dissolved in 40 ml. of ethyl acetate and treated with 1.5 g. of (+)-mandelic acid. After stirring overnight the precipitated solid was collected to give a first crop of 1.0 g. of tan solid m.p. 105°–110° C. Cooling the filtrate in ice afforded a second crop of 1.3 g. m.p. 86°–89° $[\alpha]_D^{25} = +48°$. The filtrate was labeled "filtrate C" and set aside. The first crop was combined with "solid B" above and recrystallized from ethyl acetate to give 1.65 g. of tan solid m.p. 90.5°–92° $[\alpha]_D^{25} = +52.2°$. This material was combined with the second crop and the whole recrystallized from isopropyl acetate affording 2.7 g. of tan crystalline solid m.p. 89°–92.5° C. $[\alpha]_D^{25} = +51.8°$. The latter was dissolved in 50 ml. of ethyl acetate and the resulting solution washed with saturated aqueous sodium bicarbonate, dried over anhydrous sodium sulfate and evaporated to dryness leaving 1.7 g. of product which corresponds to the dextrorotatory member of the pair of diastereomeric benzenemethanols present in the product of Example 12A. A 650-mg. sample was dissolved in isopropyl acetate and the resulting solution acidified with glacial acetic acid and evaporated to dryness. The residue was crystallized from a small volume of isopropyl acetate to give 700 mg. of the acetate salt, m.p. 70°–72° C. $[\alpha]_D^{25} = +31.3°$.

B. "Filtrate C" was evaporated to dryness. The residue was dissolved in ether-ethyl acetate and the resulting solution washed with saturated aqueous sodium bicarbonate, treated with 2 g. of decolorizing carbon, filtered and the filtrate evaporated to dryness leaving 3.8 g. of residue. This material was dissolved in 25 ml. of isopropyl acetate and the resulting solution treated with a solution containing 1.3 g. of (−)-mandelic acid in 10 ml. of isopropyl acetate. After stirring 2 days the precipitated product was collected to give 3.25 g. of white crystalline solid, m.p. 104°–106° C., $[\alpha]_D^{25} = -30.4°$. This material was combined with "solid C" above and the whole recrystallized successively from 25 ml. of ethyl acetate, 40 ml. of ethyl acetate and finally from isopropyl alcohol-ethyl acetate in each instance allowing the product to crystalline slowly at room temperature. There was thus obtained 3.5 g. of white needles m.p. 110°–111° C., $[\alpha]_D^{25} = -33.4°$. The latter was dissolved in 50 ml. of ethyl acetate, and the resulting solution washed with saturated aqueous sodium bicarbonate, dried over anhydrous sodium sulfate and evaporated to dryness to give 2.4 g. of product ($[\alpha]_D^{25} = -5.1°$) which corresponds to the levorotatory member of the pair of diastereomeric benzenemethanols present in the product of Example 12A. A 1.1-gram sample was converted to the acetate salt as described above for the dextrorotatory diastereomer affording the crystalline acetate salt as white platelets. m.p. 124°–124.5° C. $[\alpha]_D^{25} = -5.4°$.

C. A 99-gram sample of dexrorotatory 4-hydroxy-α-<{[3-(4-methoxyphenyl)-1-methylpropyl]amino}methyl>-3-(methylthio)benzenemethanol acetate salt (m.p. 129°–130° C., $[\alpha]_D^{25} = +7.1°$) prepared as described in Example 12C was treated with aqueous sodium carbonate and the free base was extracted into 1 liter of ethyl acetate. The ethyl acetate solution was washed with water and saturated aqueous sodium chloride, dried over anhydrous sodium sulfate and evaporated to dryness. The residual oil was dissolved in hot ether and the solution was filtered through a 1-inch pad of silica gel in order to remove a colored impurity. Evaporation of the ether left 83 g. of a pale yellow gum which was dissolved in 200 ml. of ethyl acetate and treated with a solution containing 22 g. of (+)-mandelic acid in 200 ml. of ethyl acetate. The mixture was stirred overnight at room temperature and then overnight at 5° C. The precipitated product was collected by filtration and washed with isopropyl acetate and ether. The mother liquors were set aside. The collected solid was recrystallized from isopropyl acetate containing a small amount of 2-propanol to give 27 g. of product m.p. 89°–91° C., $[\alpha]_D^{25} = +49.4°$. The mother liquors which had been set aside were reconverted to the free base and again treated with 20 g. of (+)-mandelic acid to give after two recrystallizations from isopropyl acetate and one from ethyl acetate and an additional 6.0 g. of product $[\alpha]_D^{25} = +47.6°$. The mother liquors from this second treatment with (+)-mandelic acid were enriched in the levorotatory diastereomer and were set aside for use in part D. The solids were combined and recrystallized twice from ethyl acetate to give 22 g. of the (+)-mandelate salt, m.p. 94°–95.5° C. $[\alpha]_D^{25} = +54.0°$. This salt was treated with 80 ml. of 10% aqueous sodium carbonate and the free base extracted into 300 ml. of ethyl acetate. The ethyl acetate solution was washed with saturated aqueous sodium chloride, dried over anhydrous sodium sulfate and acidified with 2 ml. of acetic acid. The solution was concentrated and the resulting precipitate was collected and recrystallized from ethyl acetate containing a few drops of acetic acid to give 4.3 g. of 4-hydroxy-α-<{[3-(4-methoxyphenyl)-1-methylpropyl]amino}methyl>-3-(methylthio)benzenemethanol acetate salt, m.p. 133°–134° C., $[\alpha]_D^{25} = +33.3°$, corresponding to the dextrorotatory member of the pair of diastereomeric benzenemethanols present in the product of Example 12C.

A sample of this material was reacted with p-toluenesulfonyl chloride in the presence of sodium hydroxide to afford the corresponding 4-p-toluenesulfonate acetate salt m.p. 90°–92° $[\alpha]_D^{25} = +23.0°$ which was shown by high pressure liquid chromatography to have an isomeric purity ≧99%.

D. The mother liquors from part C which were enriched in the levorotatory diastereomer were combined and evaporated to dryness. The residue was treated with aqueous sodium carbonate and the free base extracted into ethyl acetate. Evaporation of the ethyl acetate left 58 g. of oil. This material was dissolved in 200 ml. of ethyl acetate, treated with a solution containing 20 g. of (−)-mandelic acid in 200 ml. of ethyl acetate and the resulting mixture stirred overnight. The precipitated salt was collected and recrystallized successively from acetone-ether, ethyl acetate, and eight times from methylene chloride-ethyl acetate to give 23 g. of incompletely resolved (as determined by thin layer chromatography) (−)-mandelate salt, m.p. 116°–117° C., $[\alpha]_D^{25} = -37.1°$ which was converted by a conventional procedure to the acetate salt $[\alpha]_D^{25} = -10.6°$. Chromatography of a 5.5-gram sample of the latter on a column of silica gel and elution with 7% methanol in ethyl acetate failed to substantially further purify the acetate salt. A 2.6-gram fraction of material which had been eluted from the column was stirred with 25 ml. of 35% aqueous sodium hydroxide and the mixture treated dropwise over 15 minutes with a solution containing 1.33 g. of p-toluenesulfonyl chloride in 30 ml. of acetone. Over the next 5 minutes the reaction mixture was treated with two additional 150-mg. portions of p-toluenesulfonyl chloride. The acetone layer was separated, diluted with an equal volume of isopropyl acetate, washed with water followed by saturated aqueous sodium chloride, and evaporated to dryness. The residue was dissolved in ethyl acetate and the solution acidified with acetic acid. The acetate salt which precipitated was recrystallized from ethyl acetate to give 1.0 g. m.p. 115°–117° C., $[\alpha]_D^{25} = -7.9°$. The filtrate afforded an additional 0.5 g., m.p. 115°–117° C. The crops were combined and converted to 1.2 g. of the (+)-mandelate salt, m.p. 154°–156° $[\alpha]_D^{25} = +14.9°$ according to the procedure described above in part C. This material was combined with another 250 mg. m.p. 157°–158° C. $[\alpha]_D^{25} = +14.3°$ obtained in a similar run, recrystallized from ethyl acetate, and then converted by a conventional procedure to the corresponding acetate salt to give 700 ml. of isomerically pure levorotatory 4-hydroxy-α-<{[3-(4-methoxyphenyl)-1-methylpropyl]amino}methyl>-3-(methylthio)benzenemethanol-4-p-toluenesulfonate acetate salt, m.p. 117°–119° C. $[\alpha]_D^{25} = -9.6°$ corresponding to the 4-p-toluenesulfonate ester of the levorotatory member of the pair of diastereomeric benzenemethanols present in the product of Example 12C. This product was shown by high pressure liquid chromatography to have an isomeric purity ≧98%.

Attempts to cleave the p-toluenesulfonate ester in order to obtain the isomerically pure levoratatory phenol were unsuccessful, however the latter compound was obtained from the corresponding benzoate as described in Example 17 hereinbelow.

EXAMPLE 14

A. Following a procedure similar to that described in Example 6C but employing 128 g. (0.72 mole) of incompletely resolved (+)-3-(4-methoxyphenyl)-1-methylpropylamine, $[\alpha]_D^{25} = +4.4°$ (2% in water), and 120 g. (0.33 mole) of 2-bromo-4'-hydroxy-3'-(methylthio)acetophenone 4'-benzoate there was obtained a first crop of 82 g., m.p. 172°–174° C. and a second crop of 43 g., m.p. 171°–174° C. The crops were combined and a 16-gram sample was recrystallized from 95% ethanol to give 10 g. of incompletely resolved (+)-4'-hydroxy-2-{[3-(4-methoxyphenyl)-1-methylpropyl]amino}-3'-(methylthio)acetophenone 4'-benzoate hydrobromide, m.p. 174°–175° C., $[\alpha]_D^{25} = +8.4°$.

B. To a vigorously stirred solution containing 180 g. (1.0 mole) of (+)-3-(4methoxyphenyl)-1-methylpropylamine [optical purity ≧97% as indicated by nmr spectroscopy in the presence of Eu(TFC)$_3$] and 55 ml. of triethylamine in 300 ml. of N,N-dimethylformamide at −60° C. there was added over 1.5 hours a solution containing 160 g. (0.384 mole) of 2-bromo-4'-hydroxy-3'-(methylthio)acetophenone 4'-benzoate in 500 ml. of N,N-dimethylformamide. Stirring was continued an additional 0.5 hour. The reaction mixture was acidified with 48% hydrogen bromide and extracted with methylene dichloride. The organic extracts were washed with water and concentrated to about 320 ml. The concentrate was diluted with 400 ml. of isopropyl acetate and cooled. The solid which precipitated was collected and dried to give 167 g. of optically pure (+)-4'-hydroxy-2-{[3-(4-methoxyphenyl)-1-methylpropyl]amino}-3'-(methylthio)acetophenone 4'-benzoate hydrobromide, m.p. 171°–173° C., $[\alpha]_D^{25} = +11.8°$. A 7.0-gram sample was recrystallized from aqueous methanol containing a small amount of HBr to give, after drying, 5.9 g., m.p. 175°–177° C. $[\alpha]_D^{25} = +11.6°$.

EXAMPLE 15

A. To a solution containing 106 g. (0.195 mole) of incompletely resolved (+)-4'-hydroxy-2-{[3-(4-methoxypheny)-1-methylpropyl]amino}-3'-(methylthio)acetophenone 4'-benzoate hydrobromide prepared according to the procedure of Example 14A in 700 ml. of methanol at 0° C. was added over 0.5 hour 6 g. (0.16 mole) of sodium borohydride. Stirring at 0° C. was continued an additional 0.5 hour. A 150-ml. aliquot of the reaction mixture was concentrated under reduced pressure below 50° C. The concentrate was dissolved in ether and the ethereal solution was washed thoroughly with water, dried over anhydrous magnesium sulfate and evaporated to dryness. The residue was dissolved in 75 ml. of isopropyl acetate and the resulting solution was acidified with acetic acid then diluted with ether until cloudy and stirred for 3 hours. The solid which precipitated was collected by filtration, washed with isopropyl acetate and ether and dried to give 6.4 g. of 4-hydroxy-α-<{[3-(4-methoxyphenyl)-1-methylpropyl]amino}methyl>-3-(methylthio)benzenemethanol 4-benzoate acetate salt, m.p. 107°–110° C.

B. The remainder of the original reaction mixture was hydrolyzed with a solution containing 9 g. of potassium hydroxide in 100 ml. of water according to the procedure of Example 10 to give 46 g. of 4-hydroxy-α-<{[3-(4-methoxyphenyl)-1-methylpropyl]amino}methyl>-3-(methylthio)benzenemethanol acetate salt, m.p. 130°-132° C., $[\alpha]_D^{25} = +4.8°$.

C. To a solution containing 10.0 g. (0.0188 mole) of optically pure (+)-4'-hydroxy-2-{[3-(4-methoxyphenyl)-1-methylpropyl]amino}-3'-(methylthio)acetophenone 4'-benzoate hydrobromide (m.p. 171°-173° C., $[\alpha]_D^{25} = +11.8°$) in 100 ml. of methanol at 0° C. was added portionwise 380 mg. of sodium borohydride. Following the addition of several ml. of acetic acid, the mixture was evaporated to dryness. The residue was dissolved in a mixture of ethyl acetate and ether and the resulting solution was washed with saturated aqueous sodium bicarbonate, dried over anhydrous sodium sulfate, acidified with 2.5 ml. of acetic acid and evaporated to dryness. Recrystallization of the residue from isopropyl acetate-ether afforded 6 g. of 4-hydroxy-α-<{[3-(4-methoxyphenyl)-1-methylpropyl]amino}methyl>-3-(methylthio)benzenemethanol 4-benzoate acetate salt $[\alpha]_D^{25} = +6.4°$ as a dextrorotatory pair of diastereomeric benzenemethanols corresponding to the products of Example 16A and B. Another, similar run afforded a product having m.p. 101°-102.5° C., $[\alpha]_D^{25} = +7.6°$.

EXAMPLE 16

A. To a solution containing 7.4 g. of the free base derived from dextrorotatory 4-hydroxy-α-<{[3-(4-methoxyphenyl)-1-methylpropyl]amino}methyl>-3-(methylthio)benzenemethanol 4-benzoate acetate salt, $[\alpha]_D^{25} = +6.4°$ in 60 ml. of isopropyl acetate was added a solution containing 1.8 g. of (+)-mandelic acid in 20 ml. of isopropyl acetate. The resulting solution was diluted with ether until slightly turbid and stirred two days at room temperature. The precipitate was collected and the mother liquors which were enriched in the levorotatory diastereomer were set aside for use in part B below. The collected solid was recrystallized eight times from methylene chloride-ether to give 3.3 g. of the (+)-mandelate salt, m.p. 126°-127° C., $[\alpha]_D^{25} = +49.1°$ which was subsequently converted to the acetate salt to give 2.1 g. of 4-hydroxy-α-<{[3-(4-methoxyphenyl)-1-methylpropyl]amino}methyl>-3-(methylthio)benzenemethanol 4-benzoate acetate salt, m.p. 88.5°-90° C., $[\alpha]_D^{25} = +26.7°$, corresponding to the dextrorotatory member of the pair of diastereomeric benzenemethanols present in the product of Example 15B.

B. The mother liquors from part A above were converted to the free base, dissolved in isopropyl acetate, treated with 1.5 g. of (−)-mandelic acid, and the solution diluted with ether. The precipitate was collected, recrystallized once from isopropyl acetate-ether to give 2.7 g. of the (−)-mandelate salt, m.p. 120°-120.5° C., $[\alpha]_D^{25} = -35.0°$ which was subsequently converted to 4-hydroxy-α-<{[3-(4-methoxyphenyl)-1-methylpropyl]amino}methyl>-3-(methylthio)benzenemethanol 4-benzoate acetate salt, m.p. 82°-83° C., $[\alpha]_D^{25} = -10.0°$, corresponding to the levorotatory member of the pair of diastereomeric benzenemethanols present in the product of Example 15B.

EXAMPLE 17

A mixture containing 600 mg. of 4-hydroxy-α-<{[3-(4-methoxyphenyl)-1-methylpropyl]amino}methyl>-3-(methylthio)benzenemethanol 4-benzoate acetate salt (m.p. 82°-83° C., $[\alpha]_D^{25} = -10.0°$, 5 ml. of 35% aqueous sodium hydroxide and several ml. of methanol was stirred 10 minutes at room temperature, then diluted with 20 ml. of water and stirred an additional 10 minutes in a warm-water bath. The pH was adjusted to 9 with acetic acid and the methanol was evaporated under reduced pressure. The residue was extracted with ethyl acetate, and after drying over anhydrous sodium sulfate the extracts were evaporated to dryness. The residue was dissolved in isopropyl acetate, the resulting solution acidified with acetic acid and cooled. The precipitated solid was collected by filtration and dried under vacuum to give 500 mg. of 4-hydroxy-α-<{[3-(4-methoxyphenyl)-1-methylpropyl]amino}methyl>-3-(methylthio)benzenemethanol acetate salt, m.p. 117°-120° C., $[\alpha]_D^{25} = -17.0°$ (average of two determinations) corresponding to the levorotatory member of the pair of diastereomeric benzenemethanols present in the product of Example 12C.

EXAMPLE 18

To a stirred solution containing 20 g. (0.134 mole) of 1,1-dimethyl-2-phenylethylamine in 40 ml. of N,N-dimethylformamide at −50° C. was added dropwise over 15 minutes a solution containing 14.5 g. (0.048 mole) of 2-bromo-4'-hydroxy-3'-(methylthio)acetophenone 4'-acetate in 35 ml. of N,N-dimethylformamide. After the addition was complete stirring was continued an additional 1.25 hours. The reaction mixture was then treated with 3.5 ml. of 12N hydrochloric acid, diluted with 100 ml. of water and extracted thoroughly with ether. The ethereal extracts were dried over anhydrous sodium sulfate, acidified with ethanolic hydrogen chloride and cooled in a refrigerator overnight. The 12.5 g. of precipitated product was collected and combined with 6.0 g. of product obtained from a previous run and recrystallized twice from chloroform-methanol affording 15 g. of 2-[(1,1-dimethyl-2-phenylethyl)amino]-4'-hydroxy-3'-(methylthio)acetophenone 4'-acetate hydrochloride, m.p. 205° C. (dec.).

EXAMPLE 19

To a stirred suspension of 15 g. (0.037 mole) of 2-[(1,1-dimethyl-2-phenylethyl)amino]-4'-hydroxy-3'-(methylthio)acetophenone 4'-acetate hydrochloride in 200 ml. of methanol at −5° C. was added portionwise over 10 minutes 750 mg. (0.020 mole) of sodium borohydride. After stirring an additional 10 minutes the reaction mixture was brought to pH 7 with glacial acetic acid and evaporated to dryness. The residue was dissolved in ether-ethyl acetate and the resulting solution washed with saturated aqueous sodium bicarbonate. The organic layer was dried over anhydrous sodium sulfate, acidified with methanesulfonic acid and concentrated to a small volume. The concentrate was diluted with benzene and evaporated to dryness. The process was then repeated employing toluene. The resulting solid residue was recrystallized from ethanol-ether to give 12 g. of a {[(1,1-dimethyl-2-phenylethyl)amino]methyl}-4-hydroxy-3-(methylthio)benzenemethanol 4-acetate methanesulfonate, m.p. 112°-115° C.

EXAMPLE 20

A solution containing 9.5 g. (0.020 mole) of α-{[(1,1-dimethyl-2-phenylethyl)amino]methyl}-4-hydroxy-3-(methylthio)benzenemethanol 4-acetate methanesulfonate, 3 g. (0.045 mole) of potassium hydroxide and 20 ml. of water in 200 ml. of 95% ethanol was stirred overnight under nitrogen. The reaction mixture was neutralized with glacial acetic acid and concentrated to a small volume. The concentrate was diluted with saturated aqueous sodium bicarbonate and extracted with ethyl acetate. The organic extracts were dried over anhydrous sodium sulfate and concentrated to a volume of 100 ml. The concentrated solution was brought to a pale yellow color by dropwise addition of glacial acetic acid whereupon crystallization began. The product was collected by filtration and recrystallized from chloroform-methanol to give 5.1 g. of α-{[(1,1-dimethyl-2-phenylethyl)amino]methyl}-4-hydroxy-3-(methylthio)-benzenemethanol acetate salt, m.p. 165°–167° C.

EXAMPLE 21

Following a procedure similar to that described in Example 18 but using 18.3 g. (0.135 mole) of 1-methyl-2-phenylethylamine and 15 g. (0.050 mole) of 2-bromo-4'-hydroxy-3'-(methylthio)acetophenone 4'-acetate there was obtained 7.1 g. of 4'-hydroxy-2-[(1-methyl-2-phenylethyl)amino]-3'-(methylthio)acetophenone 4'-acetate hydrochloride.

EXAMPLE 22

Following a procedure similar to that described in Example 5 but using 7.4 g. (0.019 mole) of 4'-hydroxy-2-[(1-methyl-3-phenylethyl)amino]-3'-(methylthio)acetophenone 4'-acetate hydrochloride, 600 mg. 0.015 mole) of sodium borohydride and 1.1 g. of potassium hydroxide there was obtained 6.3 g. of 4-hydroxy-α-{[(1-methyl-3-phenylethyl)amino]methyl}-3-(methylthio)benzenemethanol acetate salt, m.p. 131°–132° C.

EXAMPLE 23

A. To a stirred solution containing 35 g. (0.25 mole) of o-(methylthio)phenol and 27.6 g. (0.30 mole) of propionyl chloride in 100 ml. of nitrobenzene there was added portionwise over 25 minutes 46.5 g. (0.35 mole) of aluminum chloride. The reaction was exothermic and the temperature rose to 45°–50° C. When the addition was complete the reaction mixture was stirred 2 hours at 60° C. and 1 hour at 70° C. The reaction mixture was cooled, diluted with water and extracted with ether. The ethereal extracts were dried over anhydrous sodium sulfate and evaporated to dryness in vacuo. The residual oil was adsorbed on a column of silica gel and continuously eluted with boiling methylene chloride. The eluate was evaporated to dryness and the residue recrystallized from ether giving 25 g. of crystalline product which was then triturated with ether at −65° C. to give 17 g. of pure 4'-hydroxy-3'-(methylthio)-propiophenone.

B. To a stirred solution containing 17.4 g. (0.089 mole) of 4'-hydroxy-3'-(methylthio)propiophenone, and 13 ml. (0.090 mole) of triethylamine in 200 ml. of methylene chloride there was added dropwise over 0.5 hour 7.65 g. (0.098 mole) of acetyl chloride. After the addition was complete stirring was continued an additional 2 hours. The reaction mixture was then washed successively with 3N hydrochloric acid and water and evaporated to dryness. The residual oil was dissolved in ether, treated with decolorizing carbon and filtered through a bed of silica gel. The filtrate was evaporated to dryness affording 21.4 g. of 4'-hydroxy-3'-(methylthio)propiophenone 4'-acetate as a pale yellow oil.

C. To a stirred solution containing 21.4 g. (0.088 mole) of 4'-hydroxy-3'-(methylthio)propiophenone 4'-acetate in 250 ml. of chloroform was added a solution containing 14.4 g. (0.090 mole) of bromine in 40 ml. of chloroform. After a 15-minute induction period the bromine began to be consumed. After 1 hour the reaction mixture was washed with 5% aqueous sodium bicarbonate and then water. The chloroform solution was dried over anhydrous sodium sulfate and evaporated to dryness to give 19 g. of 2-bromo-4'-hydroxy-3'-(methylthio)propiophenone 4'-acetate.

D. To a stirred solution containing 30 g. (0.185 mole) of 2-(4-methoxyphenyl)-1-methylethylamine in 150 ml. of N,N-dimethylformamide there was added dropwise 19.6 g. (0.062 mole) of 2-bromo-4'-hydroxy-3'-(methylthio)propiophenone 4'-acetate. After the addition was complete stirring was continued an additional 2 hours. The reaction mixture was then diluted with chloroform and washed successively with water, dilute hydrochloric acid and saturated aqueous sodium bicarbonate. The chloroform solution was dried over anhydrous sodium sulfate and evaporated to dryness. The residue was dissolved in ether, acidified with glacial acetic acid and cooled. The precipitated product was collected and triturated with chloroform to give 6.35 g. of 4'-hydroxy-2-{[2-(4-methoxyphenyl)-1-methylethyl]amino}-3'-(methylthio)propiophenone acetate salt, m.p. 110°–112° C.

EXAMPLE 24

To a stirred solution containing 6.2 g. (0.0148 mole) of 4'-hydroxy-2-{[2-(4-methoxyphenyl)-1-methylethyl]amino}-3'-(methylthio)propiophenone acetate salt in 100 ml. of methanol at 0° C. there was added portionwise 0.5 g. of sodium borohydride. After the addition was complete stirring was continued an additional 0.5 hour. The reaction mixture was then acidified with glacial acetic acid and evaporated to dryness. The residue was diluted with saturated aqueous sodium bicarbonate and extracted with ethyl acetate. The organic extracts were evaporated to dryness and the residue dissolved in ether. The ethereal solution was acidified with glacial acetic acid and cooled. The precipitated product was collected and dried to give 5.0 g. of 4-hydroxy-α-<{[2-(4-methoxyphenyl)-1-methylethyl]amino}ethyl>-3-(methylthio)benzenemethanol acetate salt, m.p. 160°–162° C.

EXAMPLE 25

To a stirred solution containing 16 g. (0.082 mole) of 2-(3,4-dimethoxyphenyl)-1-methylethylamine and 6 ml. (0.041 mole) of triethylamine in 60 ml. of N,N-dimethylformamide at −65° C. there was added dropwise over 0.75 hour a solution containing 12.5 g. (0.041 mole) of 2-bromo-4'-hydroxy-3'-(methylthio)acetophenone 4'-acetate in 40 ml. of N,N-dimethylformamide. After the addition was complete stirring was continued an additional hour. The reaction mixture was then made slightly acidic with 5 ml. of 12N hydrochloric acid and extracted with chloroform. The organic extracts were evaporated to dryness and the residue was dissolved in trifluoroacetic acid and treated with excess acetyl chloride. After stirring 1 hour the mixture was diluted with water and evaporated to dryness. The residue was partitioned between ethyl acetate and saturated aqueous sodium bicarbonate. The organic layer was dried over anhydrous sodium sulfate and evaporated to dryness to give 12 g. of crude 2-}[2-(3,4-dimethoxyphenyl)-1-methylethyl]amino}-4'-hydroxy-3'-(methylthio)acetophenone 4'-acetate.

EXAMPLE 26

Following a procedure similar to that described in Example 22 but using 12 g. of 2-{[2-(3,4-dimethoxyphenyl)-1-methylethyl]amino}-4'-hydroxy-3'-(methylthio)acetophenone 4'-acetate, 870 mg. of sodium borohydride and 1.4 g. of potassium hydroxide there was obtained 2.2 g. of α-<{[2-(3,4-dimethoxyphenyl)-1-methylethyl]amino}methyl>-4-hydroxy-3-(methylthio)benzenemethanol acetate salt, m.p. 141°–144° C.

EXAMPLE 27

To a stirred solution containing 19.5 g. (0.12 mole) of 1,1-dimethyl-3-phenylpropylamine in 100 ml. of N,N-dimethylformamide under nitrogen at −60° C. there was added dropwise over 0.5 hour a solution containing 12 g. (0.04 mole) of 2-bromo-4'-hydroxy-3'-(methylthio)acetophenone 4'-acetate in 40 ml. of N,N-dimethylformamide. After the addition was complete stirring was continued 1 hr. at −35° C. The reaction mixture was then acidified with 10 ml. of 12N hydrochloric acid, diluted with 150 ml. of chloroform and the resulting solution washed with water. The chloroform solution was cooled to −65° C. and diluted with ether. The resulting precipitate was collected and recrystallized from ethanol to give 12 g. of 2-[(1,1-dimethyl-3-phenylpropyl)amino]-4'-hydroxy-3'-(methylthio)acetophenone 4'-acetate hydrochloride, m.p. 188°–193° C.

EXAMPLE 28

Following a procedure similar to that described in Example 5 but using 11.0 g. (0.026 mole) of 2-[(1,1-dimethyl-3-phenylpropyl)amino]-4'-hydroxy-3'-(methylthio)acetophenone 4'-acetate hydrochloride, 750 mg. (0.02 mole) of sodium borohydride and 1.4 g. (0.026 mole) of potassium hydroxide there was obtained 9.2 g. of α-{[(1,1-dimethyl-3-phenylpropyl)amino]methyl}-4-hydroxy-3-(methylthio)benzenemethanol acetate salt, m.p. 171°–172° C.

EXAMPLE 29

A. To a stirred solution containing 65 g. (1.0 mole) of potassium cyanide and 73.7 g. (0.38 mole) of 4-(p-methoxyphenyl)-2-methyl-2-butanol in 300 ml. of n-butyl ether at 60° C. there was added dropwise over 1 hour 120 ml. of concentrated sulfuric acid. When the addition was complete stirring was continued an additional hour at 50°–55° C. The reaction mixture was then poured over 1200 g. of ice, made basic with sodium carbonate and extracted with ether. The ethereal extracts were dried over anhydrous sodium sulfate and evaporated to dryness. The 76.5 g. of residual oil was heated under reflux 3 hours in 175 ml. of 12N hydrochloric acid. The mixture was cooled, washed with ether, made basic with 35% aqueous sodium hydroxide and extracted with ether. The ethereal extracts were dried over anhydrous sodium sulfate and evaporated to dryness. The residual oil was distilled under reduced pressure and the fraction boiling at 161°–162° C./22 mm. was collected affording 35 g. of 1,1-dimethyl-3-(4-methoxyphenyl)propylamine.

B. Following a procedure similar to that described in Example 4 but using 29 g. (0.15 mole) of 1,1-dimethyl-3-(4-methoxyphenyl)propylamine, 15 g. (0.05 mole) of 2-bromo-4'-hydroxy-3'-(methylthio)acetophenone 4'-acetate and 10 ml. of acetyl chloride there was obtained 9.5 g. of 2-{[1,1-dimethyl-3-(4-methoxyphenyl)propyl]amino}-4'-hydroxy-3'-(methylthio)acetophenone 4'-acetate hydrochloride, m.p. 186°–190° C.

EXAMPLE 30

Following a procedure similar to that described in Example 5 but using 9.5 g. (0.021 mole) of 2-{[1,1-dimethyl-3-(4-methoxyphenyl)propyl]amino}-4'-hydroxy-3'-(methylthio)acetophenone 4'-acetate hydrochloride, 600 mg. (0.015 mole) of sodium borohydride and 1.2 g. of potassium hydroxide there was obtained 2.3 g. of α-<{[1,1-dimethyl-3-(4-methoxyphenyl)propyl]amino}methyl>-4-hydroxy-3-(methylthio)benzenemethanol acetate salt, m.p. 173°–174° C.

EXAMPLE 31

Following a procedure similar to that described in Example 4 but using 18 g. (0.12 mole) of 1-methyl-3-phenylpropylamine, 12 g. (0.04 mole) of 2-bromo-4'-hydroxy-3'-(methylthio)acetophenone 4'-acetate and 8 ml. of acetyl chloride there was obtained 8.3 g. of 4'-hydroxy-2-[(1-methyl-3-phenylpropyl)amino]-3'-(methylthio)acetophenone 4'-acetate hydrochloride.

EXAMPLE 32

Following a procedure similar to that described in Example 5 but using 8.1 g. (0.02 mole) of 4'-hydroxy-2-[(1-methyl-3-phenylpropyl)amino]-3'-(methylthio)acetophenone 4'-acetate hydrochloride, 500 mg. of sodium borohydride and 1.2 g. of potassium hydroxide there was obtained 6.2 g. of 4-hydroxy-α-{[(1-methyl-3-phenylpropyl)amino]methyl}-3-methylthio)benzenemethanol acetate salt, m.p. 140°–142° C.

EXAMPLE 33

Following a procedure similar to that described in Example 18 but using 18.2 g. (0.11 mole) of 3-(4-methoxyphenyl)propylamine and 11.2 g. (0.037 mole) of 2-bromo-4'-hydroxy-3'-(methylthio)acetophenone 4'-acetate there was obtained 9 g. of crude 4'-hydroxy-2-{[3-(4-methoxyphenyl)propyl]amino}-3'-(methylthio)acetophenone 4'-acetate hydrochloride which was suitable for use in the next step.

EXAMPLE 34

Following a procedure similar to that described in Example 5 but using 9 g. of crude 4'-hydroxy-2-{[3-(4-methoxyphenyl)propyl]amino}-3'-(methylthio)acetophenone 4'-acetate hydrochloride, 600 mg. of sodium borohydride and 2.0 g. of potassium hydroxide there was obtained 1.2 g. of 4-hydroxy-α-<{[3-(4-methoxyphenyl)propyl]amino}methyl>-3-(methylthio)benzenemethanol acetate salt, m.p. 123°–125° C.

EXAMPLE 35

A. A stirred mixture containing 64 g. (0.334 mole) of 5-(4-methoxyphenyl)-2-pentanone, 80 g. (1.77 moles) of formamide and 6 ml. of formic acid was slowly heated to 165° C. and treated dropwise over 3.5 hours with 50 ml. of formic acid while the water formed during the reaction was allowed to distill slowly. Stirring at 165° C. was continued an additional 3 hours. The reaction mixture was then cooled, diluted with 1 liter of ice and water and extracted with a mixture of ether and benzene. The organic extracts were evaporated and the residual oil was heated under reflux 1.5 hours in 130 ml. of 12N hydrochloric acid. The mixture was cooled, diluted with 300 ml. of water and washed with a mixture of ether and benzene. The aqueous layer was made basic with 35% aqueous sodium hydroxide and extracted with a mixture of ether and benzene. The organic layer was extracted with 1N hydrochloric acid, and the acidic aqueous layer made basic with 35% aqueous sodium hydroxide and extracted with an ether-benzene mixture. The extracts were dried over anhydrous sodium sulfate and the solvent evaporated in vacuo. The residual oil was distilled under reduced pressure to give 37 g. of 4-(4-methoxyphenyl)-1-methylbutylamine, b.p. 163°–166.5° C./18 mm.

B. To a stirred solution containing 15.5 g (0.08 mole) of 4-(4-methoxyphenyl)-1-methylbutylamine in 80 ml. of N,N-dimethylformamide at −60° C. there was added dropwise over 0.75 hour a solution containing 8.0 g. (0.027 mole) of 2-bromo-4'-hydroxy-3'-(methylthio)acetophenone 4'-acetate in 25 ml. of N,N-dimethylformamide. After the addition was complete stirring at −60° to −45° C. was continued an additional hour. The reaction mixture was then acidified with 48% hydrobromic acid and extracted with chloroform. The chloroform solution was diluted with 2.5 volumes of ether and cooled to −65° C. The resulting precipitate was collected, redissolved in chloroform and the resulting solution washed thoroughly with water. The chloroform solution was then dried over anhydrous sodium sulfate and evaporated to dryness to give 9 g. of crude 4'-hydroxy-2-{[4-(4-methoxyphenyl)-1-methylbutyl]amino}-3'-(methylthio)acetophenone 4'-acetate hydrobromide.

EXAMPLE 36

Following a procedure similar to that described in Example 5 but using 9 g. of crude 4'-hydroxy-2-{[4-(4-methoxyphenyl)-1-methylbutyl]amino}-3'-(methylthio)acetophenone 4'-acetate hydrobromide, 500 mg. of sodium borohydride and 1 g. of potassium hydroxide there was obtained 5.5 g. of 4-hydroxy-α-<{[4-(4-methoxyphenyl)1-methylbutyl]amino}methyl>-3-(methylthio)benzenemethanol acetate salt, m.p. 155°–157° C.

EXAMPLE 37

A. To a stirred mixture of 52.5 g. (0.253 mole) of 4-(4-methoxyphenyl)-1,1-dimethylbutyl alcohol, and 44.5 g. (0.685 mole) of powdered potassium cyanide in 200 ml. of n-butyl ether at 60° C. was added dropwise over 1 hour 80 ml. of concentrated sulfuric acid. The temperature was maintained at 60°–65° C. throughout the addition and stirring was continued at 50°–55° C. an additional hour after the addition was complete. The reaction mixture was then poured into 850 ml. of ice, made basic with 35% aqueous sodium hydroxide and extracted with ether. The ethereal extracts were evaporated to dryness and the residual oil heated under reflux 3 hours in 125 ml. of 12N hydrochloric acid. The resulting mixture was diluted with 300 ml. of water and washed with a mixture of ether and benzene. The aqueous layer was made basic with 35% aqueous sodium hydroxide and extracted with a mixture of ether and benzene. The organic layer was then extracted with 1N hydrochloric acid, the acidic aqueous layer made basic with 35% aqueous sodium hydroxide and extracted with an etherbenzene mixture. The extracts were dried over anhydrous sodium sulfate and evaporated to dryness in vacuo affording 12.2 g of 4-(4-methoxyphenyl)-1,1-dimethylbutylamine as a straw-colored oil.

B. Following a procedure similar to that described in Example 35B but using 19 g. (0.09 mole) of 4-(4-methoxyphenyl)-1,1-dimethylbutylamine and 10.0 g. (0.033 mole) of 2-bromo-4'-hydroxy-3'-(methylthio)acetophenone 4'-acetate and allowing the final product to crystallize from acetone in a refrigerator overnight, there was obtained 10.5 g. of crystalline 4'-hydroxy-2-{[4-(4-methoxyphenyl)-1,1-dimethylbutyl]amino}-3'-(methylthio)acetophenone 4'-acetate hydrobromide, m.p. 180°–181° C.

EXAMPLE 38

Following a procedure similar to that described in Example 5 but using 10.5 g. (0.021 mole) of 4'-hydroxy-2-{[4-(4-methoxyphenyl)-1,1-dimethylbutyl]amino}-3'-(methylthio)acetophenone 4'-acetate hydrobromide, 250 mg. of sodium borohydride and 1 g. of potassium hydroxide, and recrystallizing the product from methanol-ether there was obtained 4 g. of 4-hydroxy-α-<{[4-(4-methoxyphenyl)-1,1-dimethylbutyl]amino}-methyl>-3-(methylthio)benzenemethanol as the free base m.p. 179°–180° C.

EXAMPLE 39

A stirred mixture containing 7.4 g. (0.015 mole) of optically pure (+)-4'-hydroxy-2-{[3-(4-methoxyphenyl)-1-methylpropyl]amino}-3'-(methylthio)acetophenone 4'-benzoate hydrobromide and 100 ml. of 48% hydrobromic acid was heated under reflux 1.5 hours. The reaction mixture was then evaporated to dryness and the residue triturated with ethanol and isopropyl acetate to give 5.3 g. of (+)-4'-hydroxy-2-{[3-(4-hydroxyphenyl)-1-methylpropyl]amino}-3'-(methylthio)acetophenone hydrobromide.

EXAMPLE 40

A. Following a procedure similar to that described in Example 24 but employing 5.0 g. (0.012 mole) of (+)-4'-hydroxy-2-{[3-(4-hydroxyphenyl)-1-methylpropyl]amino}-3'-(methylthio)acetophenone hydrobromide and 0.455 g. of sodium borohydride, there was obtained 4.2 g. of 4-hydroxy-α-<{[3-(4-hydroxyphenyl)-1-methylpropyl]amino}-methyl>-3-(methylthio)benzenemethanol acetate salt, $[\alpha]_D^{25} = +5°$.

In another similar run employing 10.5 g. of (+)-4'-hydroxy-2-{[3-(4-hydroxyphenyl)-1-methylpropyl]amino}-3'-(methylthio)acetophenone hydrobromide and 1.0 g. of sodium borohydride, the crude product obtained by evaporation of the ethyl acetate extracts was dissolved in isopropyl acetate and acidified with cyclohexanesulfamic acid. Concentration and dilution with ethyl acetate afforded 10.6 g. of white crystalline solid. Recrystallization from acetonitrile/acetone and aqueous ethanol/acetone afforded 8.0 g. of 4-hydroxy-α-<{[3-(4-hydroxyphenyl)-1-methylpropyl]amino}-methyl>-3-(methylthio)benzenemethanol cyclohexanesulfamate, m.p. 118°–120° C.

EXAMPLE 41

A. To a stirred solution containing 100 g. (0.55 mole) of 4'-hydroxy-3'-(methylthio)acetophenone in 650 ml. of dioxane and 300 ml. of ether was added dropwise over 4 hours a solution containing 147 g. of dioxane dibromide in 1050 ml. of 1:1 dioxane-ether. When the addition was complete the reaction mixture was diluted with 500 ml. of ether and washed with water. The organic layer was separated, washed with saturated aqueous sodium chloride, filtered through cotton and the solvents evaporated under vacuum. The residue was twice slurried in benzene and the benzene evaporated. The final residue was crystallized from benzene-ether to give after drying, 107.5 g. of 2-bromo-4'-hydroxy-3'-(methylthio)acetophenone.

B. To a stirred solution containing 50 g. (0.28 mole) of (−)3-(4-methoxyphenyl)-1-methylpropylamine(optical purity≧94% in 150 ml. of N,N-dimethylformamide at −60° C. was added dropwise over 0.5 hr. a solution containing 30 g. (0.12 mole) of 2-bromo-4'-hydroxy-3'-(methylthio)acetophenone in 80 ml. of N,N-dimethylformamide. After addition was complete, stirring at −60° C. to −40° C. was continued an additional 5.5 hours. The reaction mixture was then acidified with 60 ml. of 48% hydrobromic acid, diluted with 150 ml. of water and washed with ether. The aqueous solution was evaporated to dryness under vacuum. The residue was dissolved in dichloromethane and the resulting solution was washed with water and saturated aqueous sodium chloride. The dichloromethane was evaporated and the residue was diluted with 2-propanol and cooled to 0° C. The solid which precipitated was collected to give 9.5 g. of white crystalline hydrobromide salt. Concentration of the filtrate provided an additional 2.9 g. which was converted to the hydrochloride salt in conventional fashion affording 2.5 g. of (−)-4'-hydroxy-2-{[3-(4-methoxyphenyl)-1-methylpropyl]amino}-3'-(methylthio)acetophenone hydrochloride, m.p. 195°–197° C., $[\alpha]_D^{25} = -11.4°$.

EXAMPLE 42

Following a procedure similar to that described in Example 14B but employing 25 g. of 2-bromo-4'-hydroxy-3'-(methylthio)acetophenone 4'-benzoate and 32 g. of (−)-3-(4-methoxyphenyl)-1-methylpropylamine (optical purity ≧94%), there was obtained 29.6 g. of (−)-4'-hydroxy-2-{[3-(4-methoxyphenyl)-1-methylpropyl]amino}-3'-(methylthio)acetophenone 4'-benzoate hydrobromide.

EXAMPLE 43

Following a procedure similar to that described in Example 24 but employing 9.3 g. of (−)-4'-hydroxy-2-{[3-(4-methoxyphenyl)-1-methylpropyl]amino}-3'-(methylthio)acetophenone hydrobromide and 1 g. of sodium borohydride; and precipitating the hydrochloride salt directly from the ethyl acetate extracts, there was obtained 8.4 g. of 4-hydroxy-α-<{[3-(4-methoxyphenyl)-1-methylpropyl]amino}-methyl>-3-(methylthio)benzenemethanol hydrochloride, m.p. 156°–157° C., $[\alpha]_D^{25} = -9.3°$ as a mixture of two diastereomers.

EXAMPLE 44

Following a procedure similar to that described in Example 7 but employing 29.6 g. (0.055 mole) of (−)-4'-hydroxy-2-{[3-(4-methoxyphenyl)-1-methylpropyl]amino}-3'-(methylthio)acetophenone 4'-benzoate hydrobromide, 1.55 g. (0.041 mole) of sodium borohydride and 30 ml. of 35 percent aqueous sodium hydroxide; and isolating the product as the hydrochloride salt there was obtained 18.6 g. of 4-hydroxy-α-<{[3-(4-methoxyphenyl)-1-methylpropyl]amino}methyl>-3-(methylthio)benzenemethanol hydrochloride.

EXAMPLE 45

A mixture containing 15 g. of (+)-4'-hydroxy-2-{[3-(4-methoxyphenyl)-1-methylpropyl]amino}-3'-(methylthio)acetophenone 4'-benzoate hydrobromide, 140 ml. of acetonitrile and 40 ml. of concentrated aqueous ammonia was stirred 5 minutes whereupon a solid began to precipitate. The mixture was cooled to 0° C. and the precipitated product was collected and washed with ether. Drying at 60° C. caused the product to turn to a black gum. The latter was dissolved in the methanol-ethyl acetate and filtered through silica gel. The filtrate was evaporated to dryness and the residue was dissolved in ethyl acetate. Acidification of the resulting solution with ethanolic hydrogen chloride afforded 2.5 g. of pale yellow crystalline (+)-4'-hydroxy-2-{[3-(4-methoxyphenyl)-1-methylpropyl]-amino}-3'-(methylthio)acetophenone hydrochloride.

EXAMPLE 46

2-Bromo-4'-hydroxy-3'-(methylthio)acetophenone (26.1 g., 0.1 mole) was reacted with 3,4-dimethoxyphenethylamine (45 g., 0.25 mole) essentially according to the method described in Example 41B. The product initially obtained upon evaporation of the aqueous solution was treated with hot methanol and the insoluble N,N-bis-[4-hydroxy-3-(methylthio)phenacyl]-3,4-dimethoxyphenethylamine was filtered off. The filtrate was concentrated, diluted with 2-propanol and cooled. The resulting solid was recrystallized from water, again filtering off insoluble by-product. The product thus obtained was recrystallized from aqueous ethanol, and a 5.5 gram sample was converted to the hydrochloride salt in conventional fashion affording 4.6 g. of 2-{[2-(3,4-dimethoxyphenyl)ethyl]amino}-4'-hydroxy-3'-(methylthio)acetophenone hydrochloride, m.p. 208°–212° C.

EXAMPLE 47

Following a procedure similar to that described in Example 24 but employing 13.1 g. (0.033 mole) of 2-{[2-(3,4-dimethoxyphenyl)ethyl]amino}-4'-hydroxy-3'-(methylthio)acetophenone hydrochloride and 2.0 g. (0.053 mole) of sodium borohydride; acidifying the reaction mixture with 6N hydrochloric acid and isolating the hydrochloride salt afforded 11.5 g. of α-<{[2-(3,4-dimethoxyphenyl)ethyl]amino}methyl>-4-hydroxy-3-(methylthio)benzenemethanol hydrochloride, m.p. 124°–126° C.

EXAMPLE 48

2-Bromo-4'-hydroxy-3'-(methylthio)acetophenone (25.4 g., 0.097 mole) was reacted with 3-(4-methoxyphenyl)propylamine (40 g., 0.242 mole) essentially according to the method described in Example 41B. The product initially obtained upon evaporation of the aqueous solution was treated with aqueous ethanol. The N,N-bis-[4-hydroxy-3-(methylthio)phenacyl]-3-(4-methoxyphenyl)propylamine which precipitated was filtered off. The filtrate was evaporated to dryness and the residue was crystallized from 2-propanol/ethyl acetate. The product so-obtained was triturated with hot water and the residue was crystallized from ethanol-ethyl acetate to give 6.5 g. of 4'-hydroxy-2-{[3-(4-methoxyphenyl)propyl]amino}-3'-(methylthio)acetophenone hydrobromide.

EXAMPLE 49

Following a procedure similar to that described in Example 47 but employing 6.5 1g. (0.0153 mole) of 4'-hydroxy-2-{[3-(4-methoxyphenyl)propyl]amino}-3'-(methylthio)acetophenone hydrobromide and 1.2 g. of sodium borohydride, there was obtained 5.1 g. of 4-hydroxy-α-<{[3-(4-methoxyphenyl)propyl]amino}methyl>-3-(methylthio)benzenemethanol hydrochloride, m.p. 151°–152° C.

EXAMPLE 50

Following a procedure similar to that described in Example 41B but employing 61 g. (0.29 mole) of mescaline and 28 g. (0.107 mole) of 2-bromo-4'-hydroxy-3'-(methylthio)acetophenone there was obtained 33 g. of crystalline product contaminated with a small amount of N,N-bis-[4-hydroxy-3-(methylthio)phenacyl]-3,4,5-trimethoxyphenethylamine. The product was taken up in boiling water and the insoluble by-product was filtered off. Concentration of the filtrate to a small volume produced 18.2 g. of 4'-hydroxy-3'-(methylthio)-2-{[2-(3,4,5-trimethoxyphenyl)ethyl]amino}acetophenone hydrobromide. The hydrochloride isolated as the monohydrate had m.p. 193°–195° C.

EXAMPLE 51

Following a procedure similar to that described in Example 24 but employing 16 g. of 4'-hydroxy-3'-(methylthio)-2-{[2-(3,4,5-trimethoxyphenyl)ethyl]amino}acetophenone hydrobromide and 2.5 g. of sodium borohydride; and isolating the product as the hydrochloride there was obtained 14.6 g. of 4-hydroxy-3-(methylthio)-α-<{[2-(3,4,5-trimethoxyphenyl)ethylamino}methyl>benzenemethanol hydrochloride, m.p. 168°–169.5° C.

Additional examples of 3-(lower alkylthio)benzenemethanols and aminoalkyl 3-(lower alkylthio)phenyl ketones having respectively Formulas I and II hereinabove and which, it is contemplated, can be obtained in accordance with the above-described procedures are presented in Table A hereinbelow.

Additional examples of haloketones and the corresponding parent phenyl ketones having respectively Formulas III and V hereinabove which are useful intermediates in the preparation of the aminoalkyl 3-(lower alkylthio)phenyl ketones of Formula II (Table A) and which, it is contemplated, can be prepared in accordance with the above-described procedures are presented hereinbelow in Tables B and C. The phenyl ketones of Table C can in turn be obtained in accordance with the above-described procedures by acylating the generally known o-(lower alkylthio)phenols with an appropriate acyl halide under Friedel-Crafts conditions followed by esterification or alkylation of the resulting 3-(lower alkylthio)-4-hydroxyphenyl ketones according to conventional esterification or alkylation procedures.

It will be appreciated that among the product aspects of this invention as defined hereinabove by Formula I, there are of course included the following sub-genera:

The compounds of Formula I hereinabove wherein Y is hydrogen or lower alkanoyl;

The compounds of Formula I wherein Y is hydrogen;

The compounds of Formula I wherein Y is hydrogen or lower alkanoyl, Ar is phenyl or lower alkoxyphenyl and n is 1 or 2; and The compounds of Formula I wherein Y is hydrogen, Ar is lower alkoxyphenyl and n is 2.

TABLE A

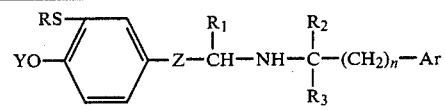

3-(Lower alkylthio)benzenemethanols
of Formula I: Z is CHOH
Aminoalkyl 3-(Lower alkylthio)phenyl
ketones of Formula II: Z is C=O

| Y | R | $R_1$ | $R_2$ | $R_3$ | n | Ar |
|---|---|---|---|---|---|---|
| H | $CH_3$ | $C_2H_5$ | H | $CH_3$ | 2 | p-$CH_3OC_6H_4$ |
| p-$CH_3C_6H_4CO$ | $CH_3$ | H | H | $CH_3$ | 2 | p-$CH_3OC_6H_4$ |
| $(CH_3)_3CCO$ | $CH_3$ | H | H | $CH_3$ | 2 | p-$CH_3OC_6H_4$ |
| HCO | $C_2H_5$ | H | H | $C_2H_5$ | 1 | $C_6H_5$ |
| $C_5H_{11}CO$ | $CH_3$ | H | H | H | 1 | $C_6H_5$ |
| H | $C_2H_5$ | H | H | $CH_3$ | 2 | p-$CH_3C_6H_4$ |
| H | n-$C_4H_9$ | H | H | $CH_3$ | 1 | m-$CH_3OC_6H_4$ |
| H | $CH_3$ | H | H | $CH(CH_3)_2$ | 1 | $C_6H_5$ |
| H | $CH_3$ | n-$C_4H_9$ | H | H | 1 | p-$(CH_3)_3CC_6H_4$ |
| H | $CH_3$ | H | $CH_3$ | $CH_3$ | 1 | 2,5-$(CH_3)_2$—$C_6H_3$ |
| H | $CH_3$ | H | H | H | 1 | p-$(CH_3)_2CHCH_2OC_6H_4$ |
| H | $CH_3$ | n-$C_3H_7$ | H | $C_4H_9$ | 1 | $C_6H_5$ |
| H | $CH_3$ | H | H | $CH_3$ | 1 | 3,4-$(HO)_2$—$C_6H_3$ |
| H | $CH_3$ | H | H | H | 1 | 3,4,5-$(HO)_3$—$C_6H_2$ |
| H | $CH_3$ | H | H | $CH_3$ | 2 | 3-Br—4-HO—$C_6H_3$ |
| H | $CH_3$ | H | H | H | 1 | 3-F—$C_6H_4$ |
| H | $CH_3$ | H | $CH_3$ | $CH_3$ | 1 | 4-Br—$C_6H_4$ |
| H | $CH_3$ | H | H | $CH_3$ | 1 | 2,5-$(Cl)_2$—$C_6H_3$ |
| H | $CH_3$ | H | H | H | 1 | 3,4,5-$(Cl)_3$—$C_6H_2$ |
| H | $CH_3$ | H | H | H | 1 | 2,4,6-$(CH_3)_3$—$C_6H_2$ |
| H | $CH_3$ | H | H | $CH_3$ | 1 | 2-$(C_4H_9O)$—3-$CH_3O$—$C_6H_3$ |

TABLE B

Intermediates

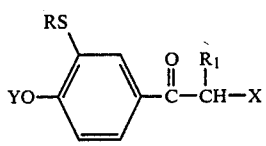

Haloketones of Formula III

| Y | R | R₁ | X |
|---|---|---|---|
| H | CH₃ | C₂H₅ | Br |
| p-CH₃C₆H₄CO | CH₃ | H | Br |
| (CH₃)₃CCO | CH₃ | H | Br |
| HCO | C₂H₅ | H | Cl |
| C₅H₁₁CO | CH₃ | H | Br |
| H | C₂H₅ | H | Br |
| CH₃CO | n-C₄H₉ | H | Cl |
| H | CH₃ | n-C₄H₉ | Br |
| H | CH₃ | n-C₃H₇ | Br |

TABLE C

Intermediates

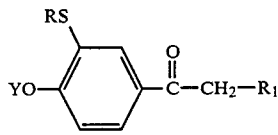

3-(Lower alkylthio)phenyl ketones of Formula V

| Y | R | R₁ |
|---|---|---|
| CH₃CO | CH₃ | C₂H₅ |
| p-CH₃C₆H₄CO | CH₃ | H |
| (CH₃)₃CCO | CH₃ | H |
| HCO | C₂H₅ | H |
| C₅H₁₁CO | CH₃ | H |
| CH₃CO | C₂H₅ | H |
| CH₃CO | n-C₄H₉ | H |
| CH₃CO | CH₃ | n-C₄H₉ |
| CH₃CO | CH₃ | n-C₃H₇ |

The compounds of this invention having Formula I have been shown to have useful antihypertensive, vasodilator and β-adrenergic blocking activity as can be seen from the results of standard pharmacological tests carried out on representative examples as described below.

Antihypertensive activity was determined on the basis of the observed reduction in systolic blood pressure measured according to the method of H. Kersten et al., J. Lab. and Clin. Med. 32, 1090 (1947) following a single oral medication in the unanesthetized spontaneous hypertensive rat described by Okamato et al., Japan Circulation J. 27, 282 (1963).

Antihypertensive activity was also judged on the basis of sustained reduction of blood pressure observed in the unanesthetized trained renal hypertensive dog following repeated oral medication according to the procedure described by Lape et al., Arch. Int. Pharmacodyn. 160, 342 (1966).

Vasodilator activity was judged on the basis of observed reduction in perfusion pressure in the hind limb vasculature of the anesthetized dog determined according to the procedure described by Jandhyala et al., European J. Pharm. 17, 357 (1972), and also on the basis of percent reduction in perfusion pressure as measured in the isolated rabbit ear artery according to the method described by De LaLande et al., Aust. J. Exp. Biol. Med. Sci. 43, 639 (1965).

The β-adrenergic blocking activity was determined in the pentobarbitalized dog as judged by the ability of the test compound to inhibit the elevation is heart rate elicited by a 0.5 mcg./kg. i.v. injection of isoproterenol.

The results of the above-described pharmacological tests are presented in Table D hereinbelow. Alsio included in Table D for purposes of comparison are test results for Reference Compounds I and II which have the following structures

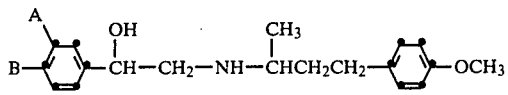

Ref. Cpd. I: A = HO, B = CH₃S
Ref. Cpd. II: A = CH₃S, B = CH₃O

Ref. Cpd.II was prepared as follows:

A. To a stirred mixture containing 116 g. (0.64 mole) of 4'-hydroxy-3'-(methylthio)acetophenone and 177 g. (1.28 moles) of potassium carbonate in 750 ml. of N,N-dimethylformamide at about 100° C. was added in a fine stream 101 g. (0.80 mole) of dimethylsulfate. When the addition was complete the mixture was stirred and heated under reflux for 2 hours, cooled and filtered. The filter cake was washed with ether and the combined filtrate and washes were evaporated to dryness under vacuum. The residue was dissolved in 3 liters of ether and the resulting solution filtered to remove a small amount of insoluble impurity. The filtrate was then evaporated to dryness, the residue was again taken up in 3.5 liters of ether, concentrated to about 500 ml. and cooled. The precipitated solid was collected and dried at 50° C. under vacuum to give 103.5 g. of 4'-methoxy-3'-(methylthio)acetophenone, m.p. 76°–77° C. Evaporation of the filtrate and recrystallization of the residue from 2-propanol afforded a second crop of 17.5 g., m.p. 76°–77° C.

B. To a cold stirred solution containing 103.5 g. (0.527 mole) of 4'-methoxy-3'-(methylthio)acetophenone in 1.1 liters of chloroform was added dropwise over a period of 3 hours a solution containing 92.5 g. (0.58 mole) of bromine in 115 ml. of chloroform. Bromination was initiated by the addition of 5 drops of ethereal hydrogen chloride. After bromine addition was complete, the reaction mixture was stirred in an ice bath for 4.5 hours. The mixture was then washed thoroughly with saturated aqueous sodium bicarbonate and dried over anhydrous sodium sulfate under nitrogen. The solvents were evaporated under vacuum and the residue was allowed to crystallize overnight at room temperature in the dark from a mixture of 610 ml. of ethyl acetate and 610 ml. of hexane. The resulting crystalline solid was collected by filtration, washed with hexane and dried at 50° C. under vacuum to give 54 g. of 2-bromo-4'-methoxy-3'-(methylthio)acetophenone, m.p. 100°–101.5° C.

C. To a stirred solution containing 35.1 g. (0.196 mole) of (+)-3-(4-methoxyphenyl)-1-methylpropylamine and 9.9 g. (0.098 mole) of diisopropylamine in 64 ml. of N,N-dimethylformamide at −55° to −60° C. was added dropwise over a period of 2.5 hours a solution containing 26.9 g. (0.098 mole) of 2-bromo-4'-methoxy-3'-(methylthio)acetophenone in 130 ml. of N,N-dimethylformamide. After the addition was complete stirring at −55° to −60° C. was continued for 1.5 hours while the temperature was maintained at −50° to −55° C. After warming to room temperature the reaction mixture was diluted with 200 ml. of water and extracted with 200 ml. of dichloromethane. The layers were separated and the organic layer was washed with water, dried over anhydrous sodium sulfate and concentrated to a thick slurry. The slurry was cooled and the precipitated solid was collected, washed with a small amount of dichloromethane and dried at 55° C. under vacuum to give 24.6 g. of (+)-4'-methoxy-2-{[3-(4-methoxyphenyl)-1-methylpropyl]amino}-3'-(methylthio)acetophenone hydrobromide, m.p. 187°–188° C. The filtrate afforded a second crop of 9.3 g., m.p. 183°–185° C.

D. To a stirred suspension containing 35.4 g. (0.081 mole) of (+)-4'-methoxy-2{[3-(4-methoxyphenyl)-1-methylpropyl]amino}-3'-(methylthio)acetophenone hydrobromide in 400 ml. of methanol at 0° C. was added portionwise over a period of 0.5 hour 3.7 g. (0.081 mole) of sodium borohydride. When the addition was complete, the reaction mixture was evaporated to dryness under vacuum and the residue partitioned between chloroform and water which was made alkaline by the addition of a small amount of sodium hydroxide. The layers were separated and the aqueous layer was extracted with fresh chloroform. The combined organic layers were then dried over anhydrous sodium sulfate and evaporated to dryness. The residue was dissolved in about 400 ml. of hot isopropyl acetate and the resulting solution was acidified with ethereal hydrogen chloride and cooled in a refrigerator overnight. The precipitated white crystalline solid was collected by filtration, washed with ether and dried at 55° C. under a vacuum. This material was combined with the product of another similar run and recrystallized three times from 2-propanol and once from ethanol to give 21.9 g. of 4-methoxy-α-<{[3-(4-methoxyphenyl)-1-methylpropyl]amino}methyl>-3-(methylthio)benzenemethanol hydrochloride, m.p. 158°–160° C., $[\alpha]_D^{25} = -8.65°$, as a levorotatory pair of diastereomeric benzenemethanols.

Ref. Cpd. I was prepared as follows:

A. To a solution containing 42 g. (0.3 mole) of o-(methylthio)phenol in 300 ml. of carbon disulfide was added over 10 min. 51.5 g. (0.66 mole) of acetyl chloride. The resulting mixture was stirred 20 min. at room temperature and then treated portionwise over 20 min. with 108 g. (0.81 mole) of anhydrous aluminum chloride and then heated under reflux for 3 hours. The reaction mixture was poured into 1 liter of ice and water containing 50 ml. of concentrated hydrochloric acid and extracted with chloroform. The chloroform extracts were washed with 3N hydrochloric acid, dried over anhydrous sodium sulfate and evaporated to dryness. The resulting solid was dissolved in 500 ml. of methylene chloride, cooled in an ice bath and treated successively with 11.8 g. (0.15 mole) of acetyl chloride and 15.2 g. (0.15 mole) of triethylamine. After stirring 0.5 hour the mixture was poured into water and the layers separated. The organic phase was washed successively with water, 3N hydrochloric acid and 10% aqueous potassium bicarbonate, dried over anhydrous sodium sulfate and evaporated to dryness. Recrystallization of the resulting solid from benzene-hexane afforded 55.7 g. of 3'hydroxy-4'(methylthio)acetophenone 3'acetate, m.p. 95.5°–97.5° C.

B. A solution containing 33.6 g. (0.15 mole) of 3'-hydroxy-4'-(methylthio)acetophenone 3'-acetate and 12.6 g. (0.13 mole) of calcium carbonate in 420 ml. of chloroform was treated with 20 drops of a solution containing 24.0 g. (0.15 mole) of bromine in 420 ml. of chloroform and the reaction mixture exposed to a sun lamp for 2 min. to initiate bromination. When the reaction had commenced, the remaining bromine solution was added over a period of 3 hours. The reaction mixture was then filtered, the filtrate washed with 200 ml. of 5% aqueous potassium bicarbonate, dried over anhydrous sodium sulfate, and evaporated to dryness. The residue was recrystallized from benzene-hexane to give 38.6 g. of 2-bromo-3'-hydroxy-4'-(methylthio)acetophenone 4'-acetate.

C. To a solution containing 21.5 g. (0.12 mole) of 3-(4-methoxyphenyl)-1-methylpropylamine in 80 ml. of DMF under nitrogen at −50° C. was added over 20 min. a solution containing 12.1 g. (0.04 mole) of 2-bromo-3'-hydroxy-4'-(methylthio)acetophenone 4'-acetate in 30 ml. of DMF. The resulting solution was stirred at −55° C. to −35° C. for 2 hours. It was then cooled to −55° C. and treated with 12 ml. of 48% hydrobromic acid and then diluted with 100 ml. of chloroform and 100 ml. of water. The precipitated product was collected by filtration, washed with water and dried to give 13.9 g. of 3'-hydroxy-2-{[3-(4-methoxyphenyl)-1-methylpropyl]amino}-4'-(methylthio)acetophenone 4'-acetate hydrobromide, m.p. 194°–197° C.

D. To a stirred solution containing 11.1 g. (0.023 mole) of 3'-hydroxy-2-{[3-(4-methoxyphenyl)-1-methylpropyl]amino}-4'-(methylthio)acetophenone 4'-acetate hydrobromide in 105 ml. of methanol was added 0.32 g. of sodium borohydride. The mixture was then cooled in ice-acetone and treated over 10 min. with an additional 0.32 g. of sodium borohydride. After stirring 15 min. a solution containing 1.5 g. (0.023 mole) of 85% potassium hydroxide in 58 ml. of water was added and the mixture heated under reflux 0.75 hour. The methanol was evaporated under vacuum and the residue acidified with 3N hydrochloric acid and then made basic with 10% potassium bicarbonate and extracted with ethyl acetate. The ethyl acetate extracts were washed with saturated aqueous sodium chloride, dried over anhydrous sodium sulfate, acidified with 4 ml. of glacial acetic acid and concentrated to a volume of about 60 ml. The resulting precipitate was collected, washed with ethyl acetate and dried to give 6.6 g. of 3-hydroxy-α-<{[3-(4-methoxyphenyl)-1-methylpropyl]amino}methyl>-4-(methylthio)benzenemethanol acetate salt, m.p. 155°–7° C.

TABLE D

| | Pharmacological Properties | | | | |
|---|---|---|---|---|---|
| | Antihypertensive Activity | | | | Adrenergic |
| | | Renal | Vasodilator Activity | | Activity |
| Cpd. of Ex. No. | SH Rat AHD$_{40}$[a] mg./kg. P.O. | Hypertensive Dog MED$_{10}$[b] mg./kg. tid | Dog-Leg Perfusion AED$_{50}$[c] mg./kg. | Rabbit Ear Artery vasodilation[d] (molar conc.) | Dog β-blockade AED$_{50}$[e] mg./kg. |
| Ref Cpd I | >50.0(−20)[f] | | | | |
| Ref Cpd II | >50.0(−24) | | | | 0.07 |
| 2 | 10.0 | | 0.5 | 50% (1 × 10$^{-5}$ M) | <1.0(60%)[h] |
| 3 | 20.0 | | 0.5 | 56% (2 × 10$^{-5}$ M) | 0.1 |
| 5 | 15.0 | >2.5(0)[g] | 0.5 | 55% (1 × 10$^{-4}$ M) | 0.1 |
| 12B | | | | | >0.1(45%) |
| 13A | | | 0.5 | | >0.1(14%) |
| 13B | | | 0.5 | | 0.1 |
| 15A | >50.0(−10)[e] | | | | |
| 20 | Ca 50.0 | | 0.5 | 71% (1 × 10$^{-5}$ M) | <1.0(56%) |
| 22 | 35.0 | | 0.5 | 33% (2 × 10$^{-5}$ M) | <1.0(60%) |
| 24 | >20.0(−23) | | | | |
| 28 | ca 10.0 | | 0.5 | 70% (5 × 10$^{-5}$ M) | <1.0(100%) |
| 30 | 20.0 | 0.5 | 0.5 | 50% (9 × 10$^{-5}$ M) | <1.0(72%) |
| 32 | 5.0 | | 0.5 | 81% (5 × 10$^{-5}$ M) | 0.1 |
| 36 | >50.0(−17) | | | | |
| 12C | | | | | Ca 0.10 |
| 40B | >50.0(−9) | | | | 0.1 |

[a]AHD$_{40}$ = single oral dose required to induce a 40 mm average reduction in systolic blood pressure in the unanesthetized spontaneous hypertensive rat.
[b]MED$_{10}$ = minimum repeated oral daily dose required to effect a sustained lowering of blood pressure of 10% or greater in the unanesthetized trained renal hypertensive dog.
[c]AED$_{50}$ = approximate intraarterial dose required to cause a 50% reduction in perfusion pressure in the hind limb of the anesthetized dog.
[d]Vasodilation is expressed as the percentage reduction in perfusion pressure from the control level at the indicated molar dose.
[e]AED$_{50}$ = approximate intravenous dose required to cause 50% inhibition of the heart rate increase elicited by isoproterenol in the pentobarbitalized dog.
[f]Actual reduction in blood pressure (in mm Hg) observed at the indicated dose.
[g]Actual precentage reduction in blood pressure observed at the indicated dose.
[h]Actual percentage inhibition of heart rate increase above control level observed at the indicated dose.

In the compounds of the present invention, especially the preferred compounds, both the nature and location of substituents are important in imparting to said compounds advantageous antihypertensive properties. For example, the antihypertensive test data given in Table D above for Example 5 and Reference Compounds I and II which have the following structures

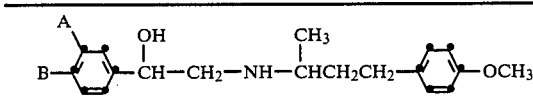

| Cpd. | A | B |
|---|---|---|
| Ex. 5 | CH$_3$S | HO |
| Ref. Cpd. I | HO | CH$_3$S |
| Ref. Cpd. II | CH$_3$S | CH$_3$O | show that the compound of Example 5, which differs from Reference Compound I solely in the relative positions of the methylthio and hydroxyl groups and from Reference Compound II solely in substitution of hydroxy for methoxy at position 3, lowers blood pressure 40 mm at a dose of 15 mg./kg. whereas Reference Compounds I and II lower blood pressure 20 and 24 mm respectively at 50 mg./kg. Thus, relative to the reference compounds, the compound of Example 5 is twice as potent at less than one-third the dose.

As noted hereinabove certain of the compounds of this invention also have antiarrhythmic activity. The latter was determined in vivo and efficacy was judged on the ability of the test compound to convert to normal rhythm the arrhythmia induced by barium ion or ouabain intoxication. The test procedures were carried out as follows:

BA++-INDUCED ARRHYTHMIA

Adult rabbits of either sex, weighing between 1.7 and 2.3 kg., were anesthetized with 30 to 35 mg./kg. Na-pentobarital i.v. via a marginal ear vein. Monopolar ECG pin electrodes were inserted for a lead II display on a Model 5 Grass Polygraph using standard electrocardiographic procedures. A 23 ga. hypodermic needle, attached via a polyethylene catheter to a 10 cc. syringe, was inserted into the same vein as was used for anesthesia. A BaCl$_2$.2H$_2$O solution in saline was then infused at a constant volume of 0.2 cc./min. from a Harvard Apparatus Model 600 infusion pump. This infusion was not stopped until termination of the experiment. In some studies barium chloride in distilled water was used without detectable differences. The standard rate of BaCl$_2$.2H$_2$O infusion was established at 0.3 mg./kg./min. (1.2×10$^{-6}$ M/kg./min.), and the concentration was adjusted appropriately in each case to accomodate the weight of the rabbit.

When the desired arrhythmia was established, the test compound was introduced as a water or saline solution into the marginal ear vein of the unused ear. The volume used was between 0.5 and 2.0 cc./kg. and was injected as a bolus over approximately 30 seconds. Deviations from standard vehicle, rate of injection and total volume administered were at the discretion of the operator. The standard initial dose of an unknown compound on the first rabbit was $5 \times 10^{-5}$ M/kg. In general two to three rabbits were used to determine anti-arrhythmic activity and the dose range of activity; multiple doses were administered. Once activity and dose was indicated, two additional rabbits were employed to confirm anti-arrhythmic activity against a multifocal tachycardia.

OUABAIN-INDUCED ARRHYTHMIA

Adult mongrel dogs of either sex, after fasting for 16 to 20 hours, were anesthetized with 35 mg./kg. Na-pentobarbital i.v. and tied supine on an operating table. A patent airway was provided by inserting an endotracheal cannula, and the animal respired spontaneously. A femoral vein was double cannulated with one cannula for injection and the other as a site for ouabain infusion. The ipsilateral femoral artery was cannulated for blood pressure measurement. Na-pentobarbital supplements were given i.v. as needed.

Statham P23A blood pressure transducers were used to measure blood pressure, and electrocardiograms (lead II or $V_1$) were taken with monopolar pin electrodes. Both parameters were printed out on a Grass polygraph. Each dog was given 36 mcg./kg. ouabain i.v. over 1 minute (the solution contained 50 mcg./ml. ouabain in isotonic saline) followed by a constant ouabain infusion (0.6 mcg./kg./min.) starting 5 minutes later. The infusion solution was prepared so that the appropriate dose per minute was delivered in 0.5 ml.

When the predominant rhythm of the ensuing arrhythmia was a ventricular tachycardia (or sometimes nodal) an attempt was made to convert this arrhythmia with the test compound. Up to $10^{-4}$ M/kg. of test drug was delivered in a volume of 1 ml./kg. over a 5 min. infusion period. If a conversion or cardiotoxic effect was seen before $10^{-4}$ M/kg. was delivered, the dose was noted and repeated on a second dog.

The test was routinely conducted using pairs of dogs with a 15 minute difference in starting time. All ECG interval and duration measurements were made on lead II with a chart speed of 100 mm./sec. Heart rates were taken from lead II QRS complexes at 25 mm./sec. Blood pressure was measured using a sensitivity of 10 mm. Hg/mm. pen deflection.

The compound of Example 12C was active at $2.5 \times 10^{-5}$ M/kg. in converting ouabain-induced arrhythmia and active at $5 \times 10^{-6}$ M/kg. in converting Ba$^{++}$-induced arrhythmia. The compound of Example 51 was active at $1 \times 10^{-5}$ M/kg. in converting Ba$^{++}$-induced arrythmia but was inactive below and toxic at $2.5 \times 10^{-5}$ Mg/kg. in the ouabain test.

I claim:

1. A compound having the formula

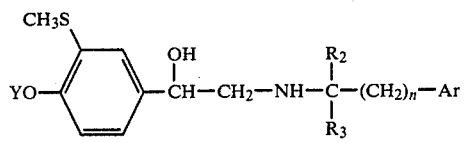

wherein
$R_2$ and $R_3$ are independently hydrogen or lower alkyl;
n is the integer 1 or 2;
Ar is lower alkoxyphenyl; and
Y is hydrogen or lower alkanoyl;
or an acid addition salt thereof.

2. A compound according to claim 1 wherein Ar is 4-methoxyphenyl.

3. A compound according to claim 2 wherein Y is lower alkanoyl.

4. A compound according to claim 2 wherein Y is hydrogen.

5. Alpha<{[1,1-dimethyl-3-(4-methoxyphenyl)-propyl]amino}-methyl>-4-hydroxy-3-(methylthio)benzenemethanol or an acid-addition salt thereof according to claim 4.

6. 4-Hydroxy-α-<{[3-(4-methoxyphenyl)-1-methyl-propyl]amino}methyl>-3-(methylthio)benzenemethanol or an acid-addition salt thereof according to claim 4.

7. The method of lowering blood pressure in a mammal which comprises administering to said mammal a blood pressure lowering effective amount of a compound according to claim 2.

8. The method of lowering blood pressure in a mammal which comprises administering to said mammal a blood pressure lowering effective amount of a compound according to claim 6.

* * * * *